(12) United States Patent
De Cola et al.

(10) Patent No.: US 10,821,082 B2
(45) Date of Patent: Nov. 3, 2020

(54) DISINTEGRATABLE CORE/SHELL SILICA PARTICLES FOR ENCAPSULATING AND RELEASING BIOACTIVE MACROMOLECULES

(71) Applicant: Universite de Strasbourg, Strasbourg (FR)

(72) Inventors: Luisa De Cola, Strasbourg (FR); Eko Adi Prasetyanto, Strasbourg (FR); Alessandro Bertucci, Parma (IT); Dedy Septiadi, Fribourg (CH)

(73) Assignee: UNIVERSITE DE STRASBOURG, Strasbourg (FR)

(*) Notice: Subject to any disclaimer, the term of this patent is extended or adjusted under 35 U.S.C. 154(b) by 268 days.

(21) Appl. No.: 15/318,189

(22) PCT Filed: Jun. 12, 2015

(86) PCT No.: PCT/EP2015/063198
§ 371 (c)(1),
(2) Date: Dec. 12, 2016

(87) PCT Pub. No.: WO2015/189402
PCT Pub. Date: Dec. 17, 2015

(65) Prior Publication Data
US 2017/0119688 A1 May 4, 2017

(30) Foreign Application Priority Data
Jun. 13, 2014 (EP) .................... 14305905

(51) Int. Cl.
| | | |
|---|---|---|
| *A61K 9/51* | (2006.01) | |
| *A61K 31/713* | (2006.01) | |
| *A61K 38/17* | (2006.01) | |
| *A61K 38/45* | (2006.01) | |
| *A61K 38/41* | (2006.01) | |
| *A61K 8/02* | (2006.01) | |
| *A61K 8/65* | (2006.01) | |
| *A61Q 19/00* | (2006.01) | |
| *A61K 31/711* | (2006.01) | |
| *A61K 8/25* | (2006.01) | |
| *A61K 38/00* | (2006.01) | |

(52) U.S. Cl.
CPC .......... *A61K 9/5123* (2013.01); *A61K 8/0279* (2013.01); *A61K 8/25* (2013.01); *A61K 8/65* (2013.01); *A61K 9/5115* (2013.01); *A61K 9/5192* (2013.01); *A61K 31/711* (2013.01); *A61K 31/713* (2013.01); *A61K 38/177* (2013.01); *A61K 38/415* (2013.01); *A61K 38/45* (2013.01); *A61Q 19/00* (2013.01); *A61K 38/00* (2013.01); *A61K 2800/10* (2013.01)

(58) Field of Classification Search
None
See application file for complete search history.

(56) References Cited

U.S. PATENT DOCUMENTS

2010/0203115 A1* 8/2010 Cronna Canos ..... A61K 9/1271
424/450

FOREIGN PATENT DOCUMENTS

EP      2 177 211      4/2010

OTHER PUBLICATIONS

Asefa, T. et al., "Periodic Mesoporous Organosilicas With Organic Groups Inside the Channel Walls", Nature, vol. 402, 1999, pp. 867-871.
Graffner-Nordberg, M. et al., "Synthesis and Enzymatic Hydrolysis of Esters, Constituting Simple Models of Soft Drugs", Chem. Pharm. Bull., vol. 46, No. 4, 1998, pp. 591-601.
Hall S.R. et al., "Cocondensation of Organosilica Hybrid Shells on Nanoparticle Templates: A Direct Synthetic Route to Functionalized Core-Shell Colloids", Langmuir, vol. 16, 2000, pp. 1454-1456.
Inagaki, S. et al.; "An Ordered Mesoporous Organosilica Hybrid Material With a Crystal-Like Wall Structure", Nature, vol. 416, 2002, pp. 304-307.
Kluck, R.M. et al., "The Release of Cytochrome c From Mitochondria: A Primary Site for Bcl-2 Regulation of Apoptosis", Science, vol. 275, 1997, pp. 1132-1136.
Kobayashi, M. et al., "Identification of Active Sites in Amidase: Evolutionary Relationship Between Amide Bond-and Peptide Bond-Cleaving Enzymes", PNAS, vol. 94, 1997, 11986-11991.
Lopreore, C. et al., "The Urease-Catalyzed Hydolysis of Thiourea and Thioacetamide", Archives of Biochemistry and Biophysics, vol. 349, No. 2, 1998, pp. 299-303.
Pyun, J. et al., "Synthesis and Characterization of Organic/Inorganic Hybrid Nanoparticles: Kinetics of Surface-Initiated Atom Transfer Radical Polymerization and Morphology of Hybrid Nanoparticle Ultrathin Films", Macromolecules, vol. 36, 2003, pp. 5094-5104.
Rowan, S.J. et al., "Dynamic Covalent Chemistry", Chem. Int. Ed., vol. 41, 2002, pp. 898.
Sanchez, C. et al., "Applications of Hybrid Organic-Inorganic Nanocomposites", J. Mater. Chem., vol. 15, 2005, pp. 3559-3592.
Shea, K.J. et al., "Bridged Polysilsesquioxanes. Molecular-Engineered Hybrid Organic-Inorganic Materials", Chem. Mater., vol. 13, 2001, pp. 3306-3319.
Corma et al., "Organic-Inorganic Nanospheres with Responsive Molecular Gates for Drug Storage and Release", Angewandte Chemie International Edition, vol. 48, No. 34, Aug. 10, 2009, pp. 6247-6250 NPL reference number: XP055153544 ISSN: 1 433-7851 DOI: 10.1002/anie.20090220 First published: Jul. 16, 2009.
Quesada et al., "Hybrid PLGA-Organosilica Nanoparticles with Redox-Sensitive Molecular Gates" Chemistry of Materials, vol. 25, No. 13, Jul. 9, 2013, pp. 2597-2602, NPL reference number: XP055153560 ISSN: 0897-4756 DOI: 10.1021/cm400700g; Publication Date (Web): Jun. 7, 2013.

(Continued)

*Primary Examiner* — James D Schultz
(74) *Attorney, Agent, or Firm* — Brinks Gilson & Lione; John C. Freeman

(57) ABSTRACT

The present invention relates to disintegratable core/shell silica particles encapsulating a bioactive macromolecule or bioactive macromolecule cluster in an active conformation, a method for producing the same, and uses thereof.

22 Claims, 16 Drawing Sheets
(10 of 16 Drawing Sheet(s) Filed in Color)

(56) References Cited

OTHER PUBLICATIONS

Fickert et al., "Silica nanocapsules for redox-responsive delivery", Colloid and Polymer Science, Nov. 12, 2013, vol. 292, Issue 1, pp. 251-255 NPL reference No. XP055153580 ISSN: 0303-402X DOI: 10.1007/s00396-013-3105-8; First Online: Nov. 12, 2013.
Quignard et al., "Introduction of disulfide bridges within silica nanoparticles to control their intra-cellular degradation" Chemical Communications, Jan. 1, 2013, vol. 49, No. 33, pp. 3410-3412 NPL Reference number: XP055153319 ISSN: 1359-7345 DOI: 10.1039/C3CC41062E; Received Feb. 7, 2013, Accepted Mar. 12, 2013 First published online Mar. 13, 2013.
Zhao et al., "Redox-responsive nanocapsules for intracellular protein delivery" Biomaterials, Mar. 25, 2011, Elsevier Science Publishers BV., Barking, GB, vol. 32, No. 22, pp. 5223-5230 ISSN: 0142-9612 DOI: http://dx.doi.org/10.1016/j.biomaterials.2011.03.060.
International Search Report dated Aug. 4, 2015 (3 pages) out of PCT priority Application No. PCT/EP2015/063198.
Written Opinion dated Aug. 4, 2015 (7 pages) out of PCT priority Application No. PCT/EP2015/063198.

* cited by examiner

| Cy-BS-NP before break | | | Cy-BS-NP after break | | |
|---|---|---|---|---|---|
| EDS Quantitative Results | | | EDS Quantitative Results | | |
| Element | Wt% | At% | Element | Wt% | At% |
| NK | 4.84 | 9.28 | NK | 48.21 | 65.51 |
| SiK | 92.63 | 88.60 | SiK | 44.52 | 30.17 |
| SK | 2.53 | 2.12 | SK | 7.27 | 4.32 |

DISINTEGRATABLE CORE/SHELL SILICA PARTICLES FOR ENCAPSULATING AND RELEASING BIOACTIVE MACROMOLECULES

PRIORITY

This application claims priority to International Application No. PCT/EP2015/063198 filed Jun. 12, 2015 and to European Application No. 14305905.3 filed Jun. 13, 2014; the entire contents of each are incorporated herein by reference.

FIELD OF THE INVENTION

The present invention relates to disintegratable core/shell silica particles, a method for producing the same, and uses thereof.

The present invention also relates to the encapsulation and release of a single or multiple biomolecules using a disintegratable silica shell. The new method allows the delivery of enzyme, proteins, oligonucleotides, and other biomolecules with the protection of the fragile biomolecules and their total release upon a stimulus which triggers the disintegration of the shell.

The present invention further relates to methods and compositions for use in the administration of biologically active macromolecules for prophylactic, therapeutic or cosmetic applications.

BACKGROUND OF THE INVENTION

The direct delivery of specific proteins to live cells promises a tremendous impact in biological and medical applications, from restoring the function of interest, producing highly specific molecules in situ, to regulating gene expression without any genomic alteration leading to a reprogramming of the cell behavior. Innovations in biotechnology and nanomedicine have led to a significant increase in the number of protein- and peptide-based therapeutics and other macromolecular drugs. Furthermore, recent advances in genomic and proteomic technologies are expected to continue to expand the pipeline of macromolecular curative candidates. As another example, several diseases are caused by the lack or low expression of important enzymes, proteins, and other biomolecules. The delivery of fragile, toxic and cell impermeable biomolecules or pharmaceutics present a serious obstacle to having an effective therapy. Drug delivery relates to administering a bio-active molecules or pharmaceutical compounds to achieve a therapeutic effect in humans or animals. In case of bio-active molecules such as protein or enzyme, a major complication in the use of this type of drugs is the difficulty of delivering the necessary site of action.

In this respect, it requires delivery system which is able to protect the bio-active molecules or pharmaceutical compound, large number of deliverable materials but also able to be functionalized further if required.

Innovations in biotechnology have led to a significant increase in the number of protein and peptide therapeutics and other macromolecular drugs. Further, recent advances in genomic and proteomic technologies are expected to continue to increase the pipeline of macromolecular therapeutic candidates.

Nevertheless, working with macromolecules typically poses a number of challenges, that drug developers must overcome in order to successfully develop these compounds into safe and effective therapeutics, not the least of which being the efficient delivery of native, functional protein or enzyme in an active conformation to the necessary site of action which still remains a challenge today. For example, in physiological conditions, proteins and peptides tend to undergo degradation by proteolytic enzymes or, in the case of the higher molecular weight proteins, may be recognized by neutralizing antibodies. Moreover, such molecules can exhibit low solubility or poor stability, leading to short shelf lives. As a result, macromolecule-based therapeutic strategies often quickly lose their effectiveness or require frequent dosing. These factors impact not only cost of therapy, but also patient acceptance and compliance, thus affecting their therapeutic usefulness. To overcome these problems, suitable delivery systems must be able to shield and protect the bioactive molecules in order to preserve their functional nature, reducing the need for repetitive injections and allowing the reach of organs without compromising the biological activity of the protein.

Thus, protein/enzyme stabilization is of great interest to a variety of applications including medical diagnostics, biocatalysis, and protein delivery. For example, protein or enzyme based medical diagnostic kits that exhibit prolonged shelflife could improve performance and significantly reduce costs.

For protein delivery applications, the protein carriers or stabilizers have to meet stringent requirements. The ideal protein carriers have to be not only non-toxic and non-immunogenic, but also must be able to protect labile proteins against natural deterioration. Moreover, in reality, the larger protein carriers (i.e. greater than 5-7 µm) are often rapidly cleared from blood by capillary filtration primarily in the lungs. The smaller carriers (i.e. less than 200 nm), although free to circulate through capillaries, still face attacks from the immune system, thus being removed from blood rapidly by phagocytosis. Therefore, those carriers that are capable of generating long-term blood circulation of proteins and drugs can provide numerous advantages such as enhancing the efficiency of drug controlled-release, providing site specific protein delivery, as well as reducing the need for repetitive injections.

Currently, protein stabilization has mainly been achieved by: 1) micro- and nano-encapsulation (i.e. within liposomes, polymeric or inorganic structures); 2) bioconjugation (i.e. covalently linking proteins with water-soluble polymers or simply crosslinking proteins to form stable particle complexes); or 3) genetic modification (i.e. genetically altering the protein sequence to make it more stable). However, the encapsulation strategy that utilizes lipid-based micelles often suffers problems such as poor solution stability (especially under extreme temperatures and pH) and difficulty in being freeze-dried. In addition, the size distribution of these micelles is also very broad. The polymer-based encapsulation strategy, although significantly improving the freeze-drying capability, has very poor solution stability since only physical interactions are present between polymers and proteins. On the other hand, by using polyethylene glycol or oxide (PEG or PEO) modified liposomes (i.e. stealth liposomes) or biodegradable/non-degradable particles (stealth particles), the protein stability can be significantly enhanced. However, the sizes of these carriers are still too large (i.e. in microns) for more efficient, accurate and intracellular delivery purposes. The bioconjugation of protein molecules with different water-soluble polymers such as PEGs and PEOs may also enhance the stability of proteins. However, this approach is very labor intensive, and, in some cases, the process can denature the proteins resulting in significant activity loss. Through proper genetic modification, the shelf-stability of proteins can be improved dramatically. Unfortunately, in most cases, the protein activity or specificity has also dropped very substantially.

At present, there is therefore a need for the development of nanoencapsulated enzymes and other nanoencapsulated bioactive macromolecules having improved stability, improved in vivo delivery characteristics, and the ability to withstand harsh environmental conditions and preserve their active conformation.

BRIEF DESCRIPTION OF THE DRAWING

The patent or application file contains at least one drawing executed as a photograph and/or in color. Copies of this patent or patent application with photographs and color drawings will be provided by the Office upon request and payment of the necessary fee.

Figure 1:
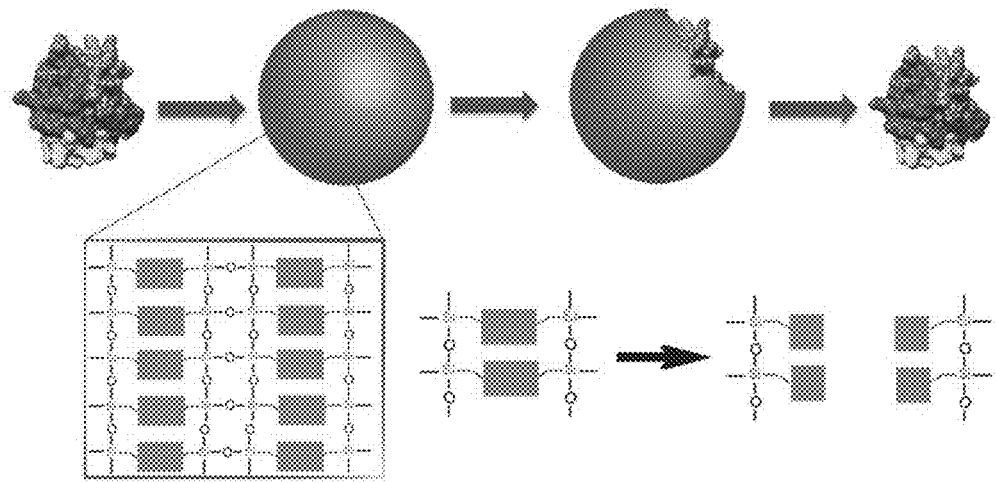
FIG. 1 represents a schematic illustration of an exemplary structure of the disintegratable hybrid organo-silica core/shell nanocapsules according to the invention, showing the presence of responsively cleavable linkers within the material's framework.
Figure 2:
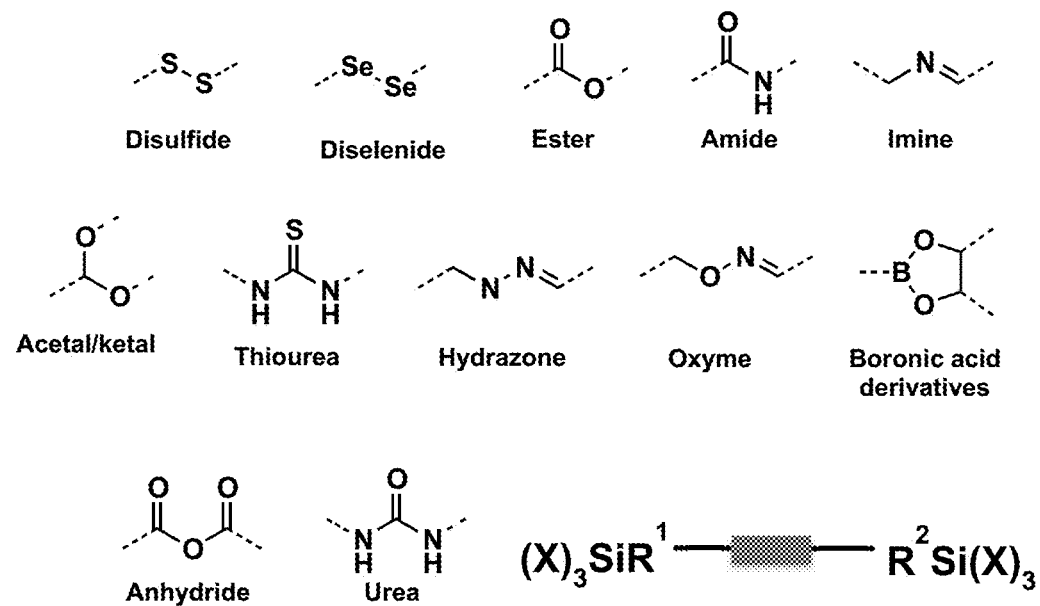
FIG. 2 represents examples of possible responsively cleavable linkers to be incorporated into the silica framework of the shell.
Figure 3:
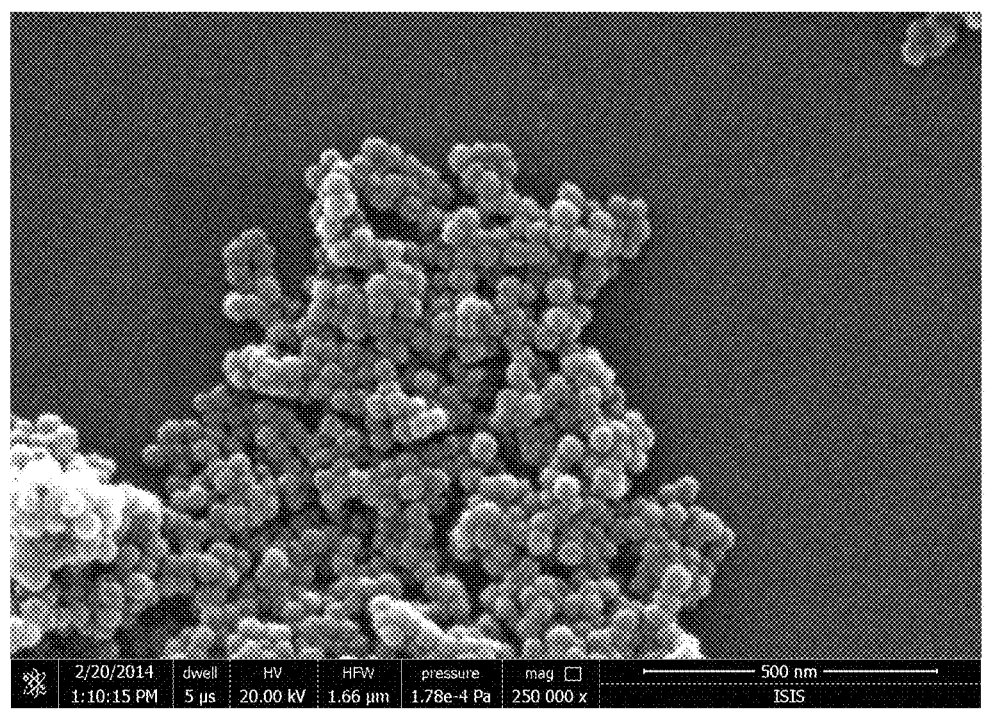
FIG. 3 represents SEM image of disintegratable silica core/shell nanoparticles encapsulating CyC according to the invention (example 1).
Figure 4:
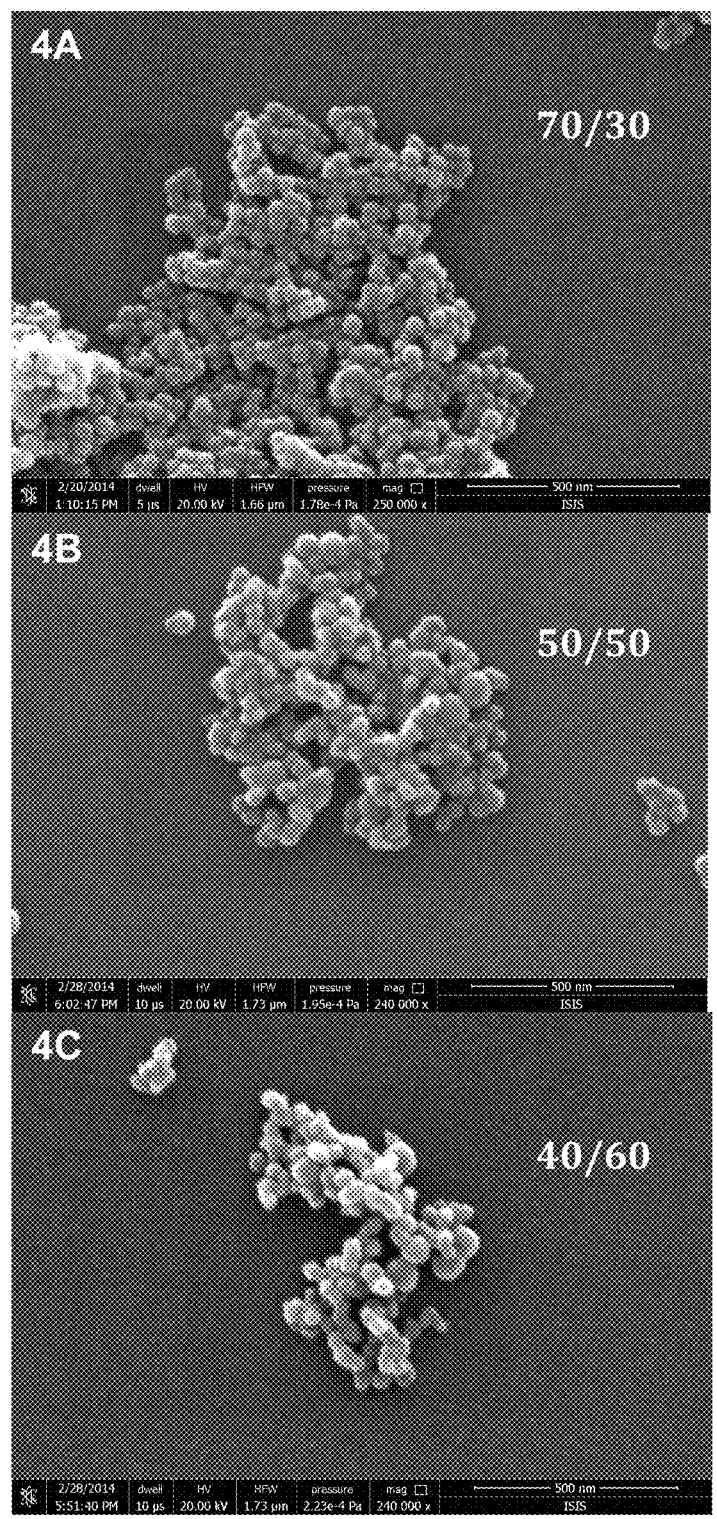
FIG. 4 represents SEM image of disintegratable silica core/shell nanoparticles encapsulating CyC with different ratio of cleavable linker.
Figure 5:
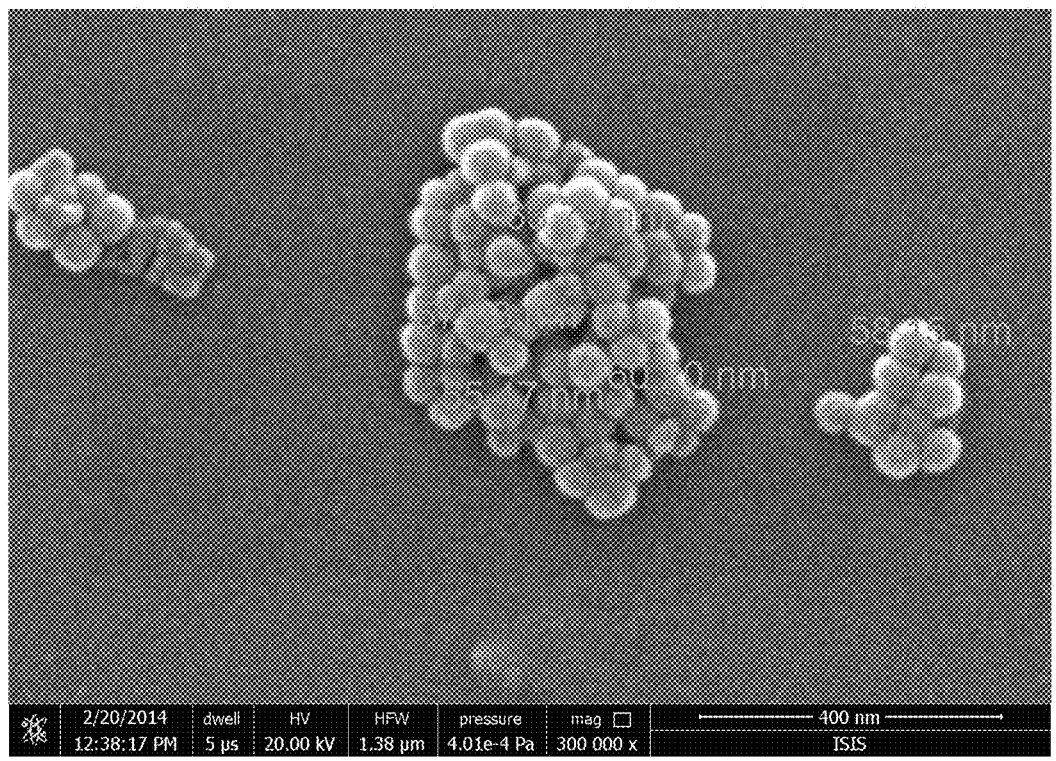
FIG. 5 represents SEM image of non-disintegratable silica core/shell nanoparticles encapsulating CyC.
Figure 6:
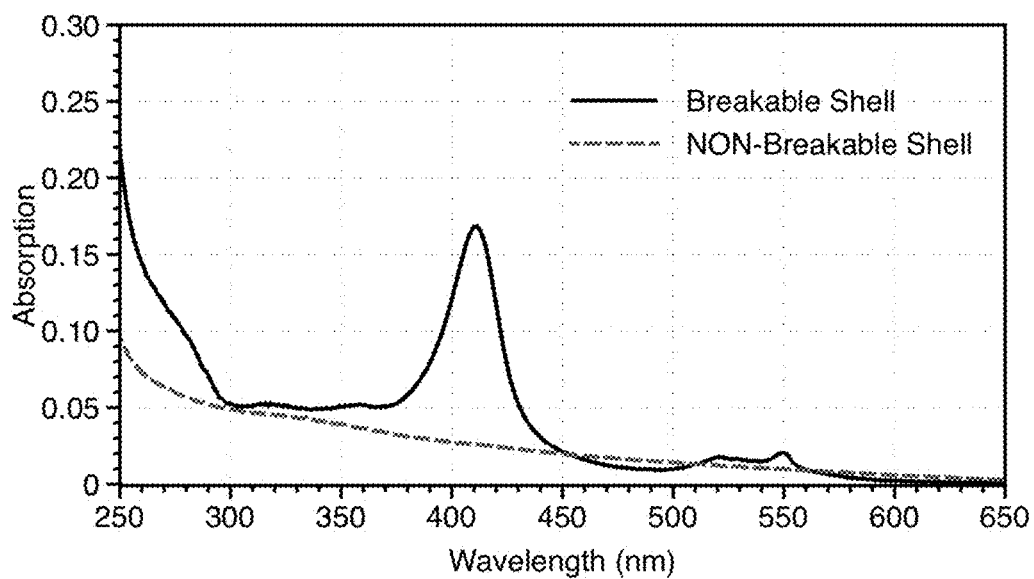
FIG. 6 represents UV-Vis spectra of protein solution and disintegratable silica core/shell nanoparticles encapsulating CyC according to the invention dispersed in water.
Figure 7:
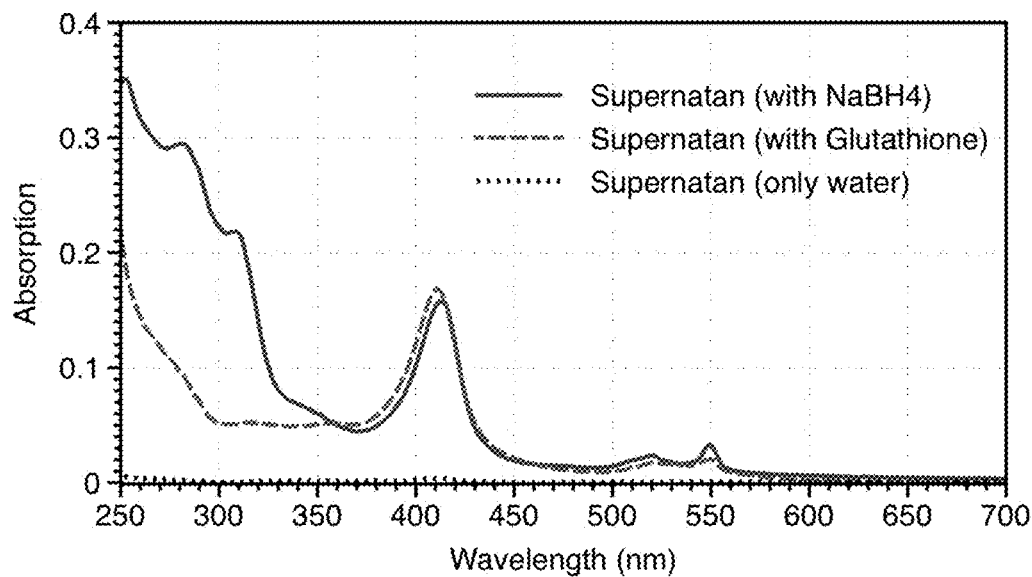
FIG. 7 represents UV-Vis spectra of supernatant of same concentration of disintegratable silica core/shell nanoparticles encapsulating CyC according to the invention in water after stirring for 24 h with and without cleaving agent (NaBH4 or Glutathione). The supernatant clearly indicated that the shell was disintegrated and release protein from the system.
Figure 8:
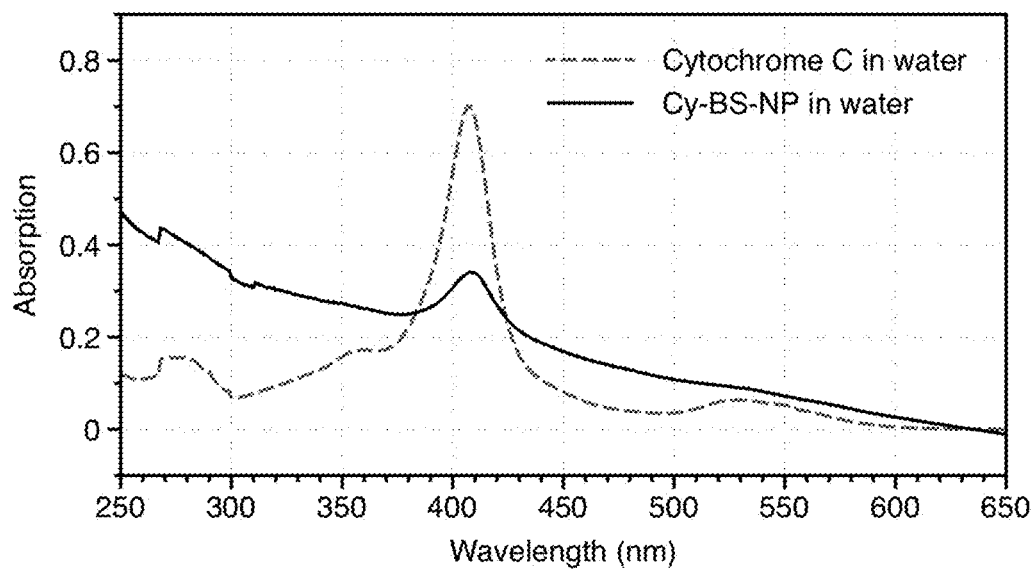
FIG. 8 represents UV-Vis spectra of supernatant of same concentration of disintegratable silica core/shell nanoparticles encapsulating CyC according to the invention and non-disintegratable silica core/shell nanoparticles encapsulating CyC in water after stirring for 24 h with breaking agent (Glutathione).
Figures 9, 10:
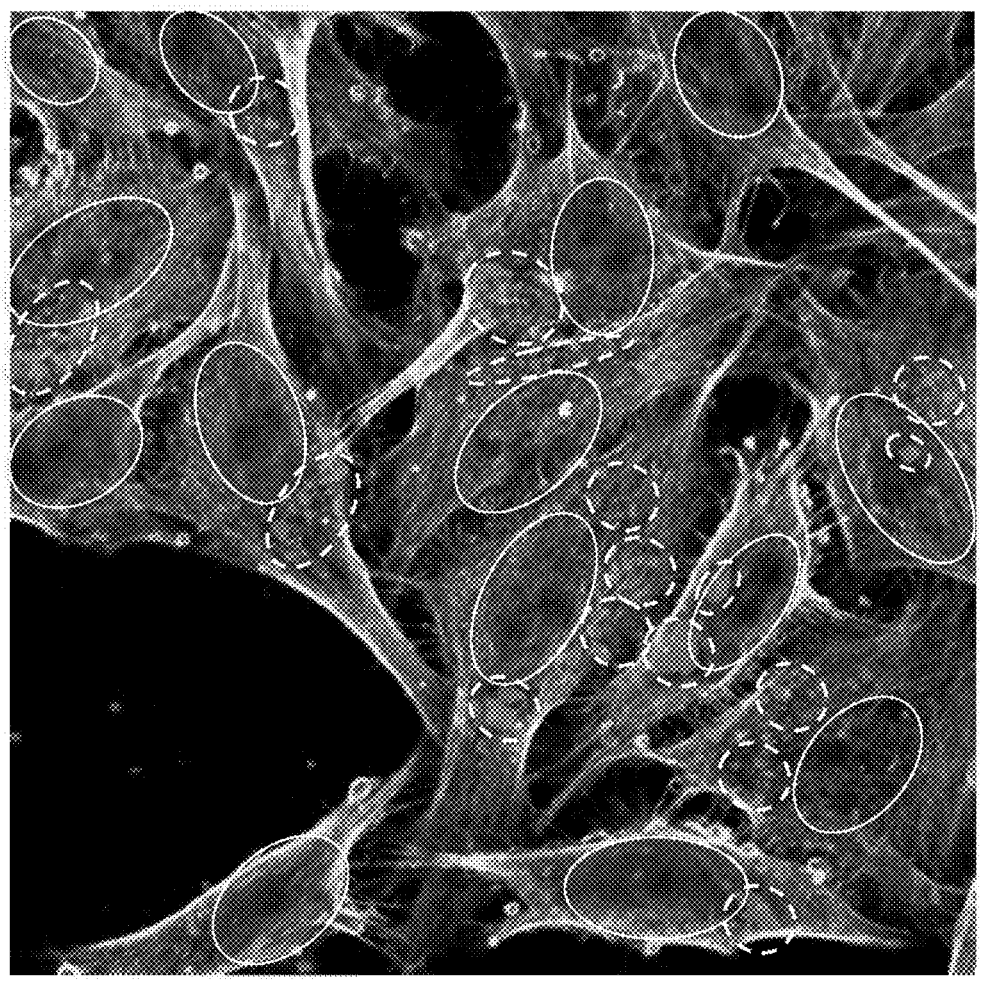
FIG. 9 represents an EDX analysis of the disintegratable silica core/shell nanoparticles encapsulating CyC according to the invention before and after disintegrating the shell.
FIG. 10 represents a confocal microscopy image of HeLa cells with internalized disintegratable silica core/shell nanoparticles encapsulating CyC according to the invention (orange colour (indicated on black & white photograph with dotted circles/ovals), signal is coming from emission of cy5 on the surface of the disintegratable shell). Plain line circles/ovals indicate blue color on the photograph.
Figure 11:
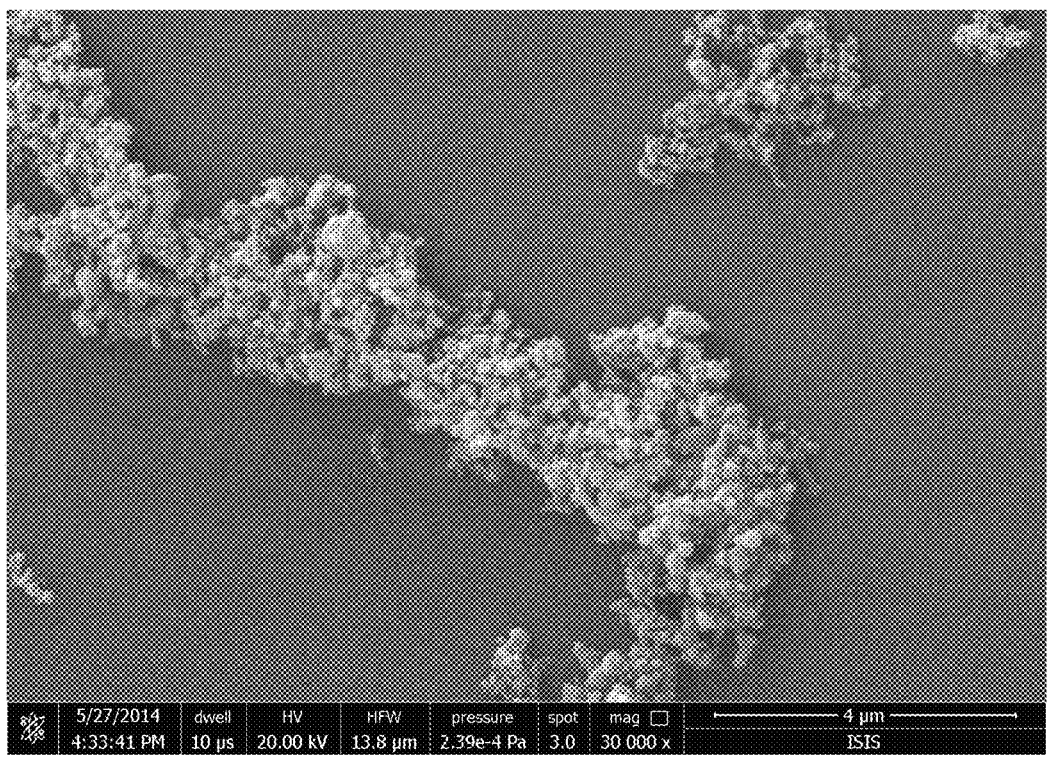
FIG. 11 represents SEM image of disintegratable silica core/shell nanoparticles encapsulating TRAIL according to the invention.
Figure 12:
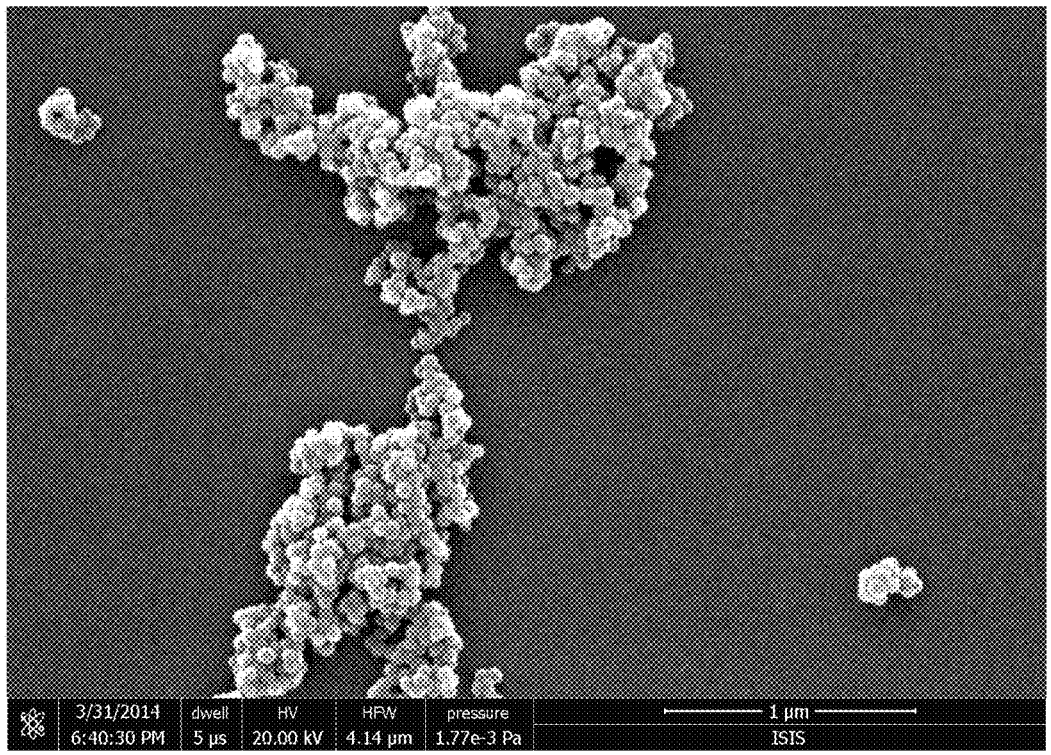
FIG. 12 represents SEM image of disintegratable silica core/shell nanoparticles encapsulating DNA according to the invention.
Figure 13:
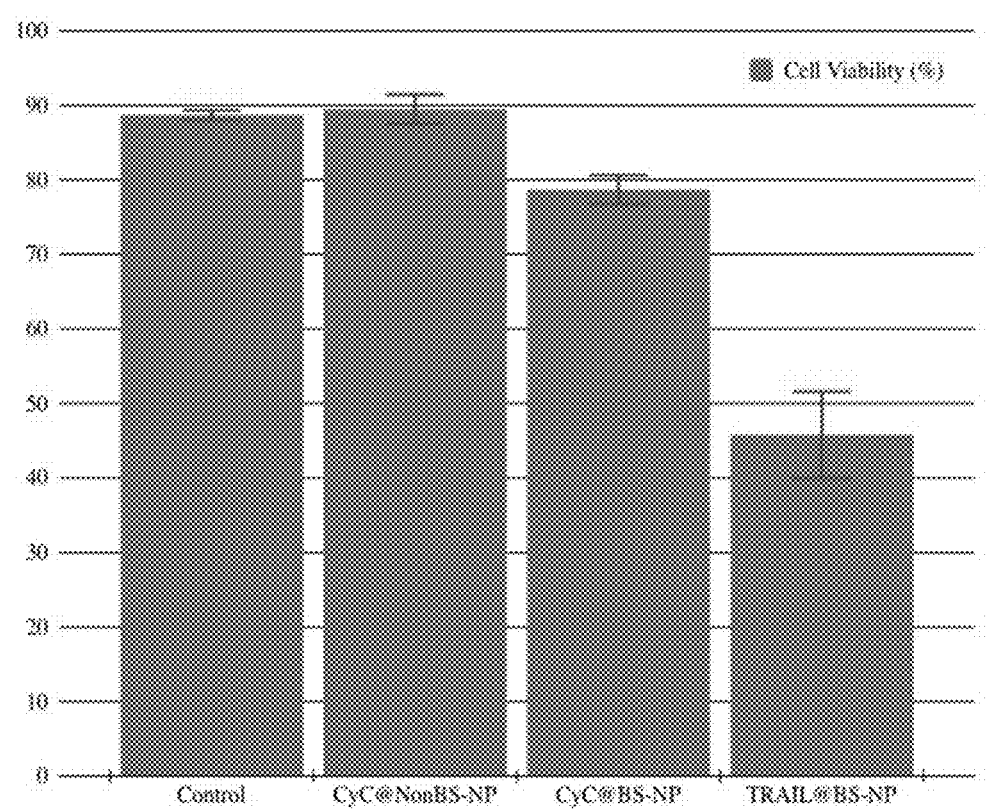
FIG. 13 represents viability of C6 Glioma cells after 24 h incubation with disintegratable silica core/shell nanoparticles encapsulating TRAIL according to the invention or disintegratable silica core/shell nanoparticles encapsulating CyC according to the invention.

Table 3 Zeta potential value of nanoparticles encapsulating CyC, TRAIL and DNA according to the invention dispersed in PBS buffer.

Table 4. Cell viability test

Definitions

To facilitate an understanding of the present invention, a number of terms and phrases are defined below:

As used herein other than the claims, the terms "a," "an," "the," and/or "said" means one or more. As used herein in the claim(s), when used in conjunction with the words "comprise," "comprises" and/or "comprising," the words "a," "an," "the," and/or "said" may mean one or more than one. As used herein and in the claims, the terms "having," "has," "is," "have," "including," "includes," and/or "include" has the same meaning as "comprising," "comprises," and "comprise." As used herein and in the claims "another" may mean at least a second or more. As used herein and in the claims, "about" refers to any inherent measurement error or a rounding of digits for a value (e.g., a measured value, calculated value such as a ratio), and thus the term "about" may be used with any value and/or range.

The phrase "a combination thereof" "a mixture thereof" and such like following a listing, the use of "and/or" as part of a listing, a listing in a table, the use of "etc" as part of a listing, the phrase "such as," and/or a listing within brackets with "e.g.," or i.e., refers to any combination (e.g., any sub-set) of a set of listed components, and combinations and/or mixtures of related species and/or embodiments described herein though not directly placed in such a listing are also contemplated. Such related and/or like genera(s), sub-genera(s), specie(s), and/or embodiment(s) described herein are contemplated both in the form of an individual component that may be claimed, as well as a mixture and/or a combination that may be described in the claims as "at least one selected from," "a mixture thereof" and/or "a combination thereof."

In general, the term "substituted" whether preceded by the term "optionally" or not, and substituents contained in formulae of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds.

As used herein, the term "alkyl", refers to straight and branched alkyl groups. An analogous convention applies to other generic terms such as "alkenyl", "alkynyl" and the like. In certain embodiments, as used herein, "lower alkyl" is used to indicate those alkyl groups (substituted, unsubstituted, branched or unbranched) having about 1-6 carbon atoms. Illustrative alkyl groups include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like. The term "$C_{1-x}$alkylenyl", as used herein, refers to a linear or branched saturated divalent radical consisting solely of carbon and hydrogen atoms, having from one to x carbon atoms, having a free valence "—" at both ends of the radical. Likewise, the term "$C_{1-x}$heteroalkylenyl", as used herein, refers to a linear or branched saturated divalent $C_{1-x}$alkylenyl radical as defined above, comprising at least one heteroatom selected from O, N, or S, and having a free valence "—" at both ends of the radical. When the $C_{1-x}$alkylenyl or $C_{1-x}$heteroalkylenyl is optionally substituted, at least one of the H atoms may be replaced by a substituent such as halogen or —OR where R may represent C1-6alkyl.

The term "ethenylenyl", as used herein, refers to the divalent radical —CH═CH—. When the ethylenyl is optionally substituted, one or both the H atoms may be replaced by a substituent such as halogen or —OR where R may represent C1-6alkyl.

In general, the term "aromatic moiety" or "aryl", as used herein, refers to stable substituted or unsubstituted unsaturated mono- or polycyclic hydrocarbon moieties having preferably 3-14 carbon atoms, comprising at least one ring satisfying the Hackle rule for aromaticity. Examples of aromatic moieties include, but are not limited to, phenyl, indanyl, indenyl, naphthyl, phenanthryl and anthracyl.

The term "halogen" as used herein refers to an atom selected from fluorine, chlorine, bromine and iodine.

As used herein, the term "independently" refers to the fact that the substituents, atoms or moieties to which these terms refer, are selected from the list of variables independently from each other (i.e., they may be identical or the same).

As used herein, the term "about" can refer to a variation of ±5%, ±10%, ±20%, or ±25%, of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As used herein, the term "and/or" means any one of the items, any combination of the items, or all of the items with which this term is associated.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible subranges and combinations of subranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to," "at least," "greater than," "less than," "more than," "or more," and the like, include the number recited and such terms refer to ranges that can be subsequently broken down into subranges as discussed above. In the same manner, all ratios recited herein also include all subratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes medical, therapeutic, and/or prophylactic administration, as appropriate. The term "responsively disintegratable", when referring to the shell of the nanocapsule system according to the invention, refers to the property of a material or particle that undergoes degradation (i.e., breakdown of the structural integrity of the material or particle) triggered by a particular signal. The signal can be, for example, a change in pH (either an increase or decrease), a change in redox potential, the presence of reduction or oxidation agent, the presence of UV, visible or near infrared light, ultrasounds, electromagnetic radiation, an enzymatic cleavage, a change in temperature, etc. The term "responsively cleavable", when referring to a chemical bond, polymer fragment or linking group, refers to a covalent bond, polymer fragment or linking group that is cleaved upon application of one of the aforementioned particular signals. Generally speaking, the presence of a responsively cleavable bond, polymer fragment or linker moiety within a hybrid organosilica nanocapsule shell of the invention, confers to the nanocapsule shell its disintegratable properties (the property of structurally breaking down upon application of a specific signal/stimulus, akin to "self-destructive" behavior). As used herein, the term "surfactant" refers to any compound that, when dissolved in a liquid, reduces surface tension of the liquid, which reduces interfacial tension between two liquids or which reduces surface tension between a liquid and a solid. More typically the term "surfactant" is used herein to refer to a compound that, when dissolved in water, reduces the surface tension of water. Advantageously, surfactants suitable in the context of the present invention are not capable of forming stable liposomes. Preferably, the surfactant has a packing parameter (P) outside the range ½ to 1. Preferably, the surfactant is not a phospholipid. As used herein, the term "hybrid organosilica framework material", "organosilica framework material" or "organosilica framework" refers to an organosilica matrix in which a $(X_3Si)R^1$—L—$R^2(SiX_3)$-type responsively cleavable linker is inserted.

As used herein, the term "linker" refers to a responsively cleavable moiety *—$R^1$—L—$R^2$—*, inserted into the hybrid organosilica framework by reaction of a $(X)_3SI$—$R^1$-L-$R^2$—$Si(X)_3$ precursor, by sol-gel chemistry (hydrolysis or condensation), with the linker being bound to the framework via two or more Si atoms in the framework. In other words, at least one X on each occurrence of Si on the precursor is hydrolyzed to lead to formation of the metaloxide framework.

As used herein, the term "cleavable" refers both to the reversible/biodegradable nature of the *—$R^1$—L—$R^2$—* linker, as defined herein, triggering the decomposition/disintegration of the bulk hybrid organosilica framework material.

As such, the linker may contain a dynamic covalent bond.

As used herein, the term "dynamic covalent bond" refers to any covalent chemical bond possessing the capacity to be formed and broken under equilibrium control. In this sense, they can be intended as "reversible" covalent bonds. [1]

As used herein, a "bioactive macromolecule" refers to a macromolecular biomolecule in an undenatured state, which still shows a conformation suited to carry on its supposed biological activity. Advantageously, "bioactive" means that the macromolecular biomolecule remains in a folded position and retains an active conformation. In other words, the macromolecular biomolecule is in biologically active form (i.e., in an active conformation to carry out its biological function).

As used herein, a "biomolecule" refers to a molecule (e.g., a compound) comprising of one or more chemical moiety(s) ["specie(s)," "group(s)," "functionality(s)," "functional group(s)"] typically synthesized in living organisms, including but not limited to, polynucleotides (RNA and DNA), which are long polymers composed of 13 or more nucleotide monomers; polypeptides, which are short polymers of amino acids; proteins; and polysaccharides, which are often linear bonded polymeric carbohydrate structures, or a combination thereof. Examples of a macromolecule includes, an enzyme, an antibody, a receptor, a transport protein, structural protein, a prion, an antibiological proteinaceous molecule (e.g., an antimicrobial proteinaceous molecule, an antifungal proteinaceous molecule), or a combination thereof.

As used herein a "proteinaceous molecule," proteinaceous composition," and/or "peptidic agent" comprises a polymer formed from an amino acid, such as a peptide (i.e., about 3 to about 100 amino acids), a polypeptide (i.e., about 101 or more amino acids, such as about 50,000 or more amino acids), and/or a protein. As used herein a "protein" comprises a proteinaceous molecule comprising a contiguous molecular sequence of three amino acids or greater in length, matching the length of a biologically produced proteinaceous molecule encoded by the genome of an organism. Examples of a proteinaceous molecule include an enzyme, an antibody, a receptor, a transport protein, a structural protein, or a combination thereof. Examples of a peptide (e.g., an inhibitory peptide, an antifungal peptide) of about 3 to about 100 amino acids (e.g., about 3 to about 15 amino acids). A peptidic agent and/or proteinaceous molecule may comprise a mixture of such peptide(s) (e.g., an aliquot of a peptide library), polypeptide(s) and/or protein(s), and may also include materials such as any associated stabilizer(s), carrier(s), and/or inactive peptide(s), polypeptide(s), and/or protein(s).

In some embodiments, a proteinaceous molecule comprises an enzyme. A proteinaceous molecule that functions as an enzyme, whether identical to the wild-type amino acid sequence encoded by an isolated gene, a functional equivalent of such a sequence, or a combination thereof, may be used. As used herein, a "wild-type enzyme" refers to an amino acid sequence that functions as an enzyme and matches the sequence encoded by an isolated gene from a natural source. As used herein, a "functional equivalent" to the wild-type enzyme generally comprises a proteinaceous molecule comprising a sequence and/or a structural analog of a wild-type enzyme's sequence and/or structure and functions as an enzyme. The functional equivalent enzyme may possess similar or the same enzymatic properties, such as catalyzing chemical reactions of the wild-type enzyme's EC classification; and/or may possess other enzymatic properties, such as catalyzing the chemical reactions of an enzyme related to the wild-type enzyme by sequence and/or structure. An enzyme encompasses its functional equivalents that catalyze the reaction catalyzed by the wild-type form of the enzyme (e.g., the reaction used for EC Classification). For example, the term "lipase" encompasses any functional equivalent of a lipase (i.e., in the claims, "lipase" encompasses such functional equivalents, "human lipase" encompasses functional equivalents of a wild-type human lipase, etc.) that retains lipase activity (e.g., catalyzes the reaction: triacylglycerol+$H_2O$=diacylglycerol+a carboxylate), though the activity may be altered (e.g., increased reaction rates, decreased reaction rates, altered substrate preference, etc.). Examples of a functional equivalent of a wild-type enzyme are described herein, and include mutations to a wild-type enzyme sequence, such as a sequence truncation, an amino acid substitution, an amino acid modification, and/or a fusion protein, etc., wherein the altered sequence functions as an enzyme. As used herein, the term "derived" refers to a biomolecule's (e.g., an enzyme) progenitor source, though the biomolecule may comprise a wild-type and/or a functional equivalent of the original source biomolecule, and thus the term "derived" encompasses both wild-type and functional equivalents. For example, a coding sequence for a *Homo sapiens* enzyme may be mutated and recombinantly expressed in bacteria, and the bacteria comprising the enzyme processed into a biomolecular composition for use, but the enzyme, whether isolated and/or comprising other bacterial cellular material(s), comprises an enzyme "derived" from *Homo sapiens*. In another example, a wild-type enzyme isolated from an endogenous biological source, such as, for example, a *Pseudomonas putida* lipase isolated from *Pseudomonas putida*, comprises an enzyme "derived" from *Pseudomonas putida*. In some cases, a biomolecule may comprise a hybrid of various sequences, such as a fusion of a mammalian lipase and a non-mammalian lipase, and such a biomolecule may be considered derived from both sources. Other types of biomolecule(s) (e.g., a ribozyme, a transport protein, etc.) may be derived, isolated, produced, in a wild-type or a functional equivalent form. In other aspects, a biomolecule may be derived from a non-biological source, such as the case of a proteinaceous and/or a nucleotide sequence engineered by the hand of man. For example, a nucleotide sequence encoding a synthetic peptide sequence from a peptide library may be recombinantly produced, and may thus "derived" from the originating peptide library.

Advantageously, the selection of a biomolecule for use will depend on the property to be conferred to a nanocapsule according to the invention. In exemplary embodiments, a biomolecule may comprise an enzyme, to confer a property such as as enzymatic activity to a material formulation (e.g., a surface treatment, a filler, a biomolecular composition). As used herein, the term "enzyme" refers to a molecule that possesses the ability to accelerate a chemical reaction, and comprises one or more chemical moiety(s) typically synthesized in living organisms, including but not limited to, an amino acid, a nucleotide, a polysaccharide, a simple sugar, a lipid, or a combination thereof.

An enzyme catalyzes a chemical reaction by converting substrate(s) ["reactant(s)"] into product(s) via an enzyme-substrate complex. The enzyme's catalytic site ("active site"), which typically comprises approximately ten amino acid residues, solvates the reactant(s) to form an enzyme-substrate complex. Subsequent dissociation of the enzyme-substrate complex forms product(s) and free enzyme upon conversion. The conformation of the active site is similar to the conformation of the reactant's transition state that forms as the reaction proceeds from reactant(s) to product(s) (or vice versa). The progression from reactant(s) to a transition state is favored by non-covalent stabilization within the active site via hydrogen bonding and/or electrostatic interaction(s). The binding energy between the enzyme active site and the bound intermediate molecule accounts for the loss of activation entropy as a consequence of reduced translational and rotational motion(s). The three dimensional conformation of the enzyme active site promotes the binding conformation between the enzyme and the intermediate state of the reaction. Enzymes lower the activation energy proportional to the binding energy of the forward and reverse reactions. According to exemplary embodiments of the present invention, nanoencapsulated enzyme systems prepared according to the method of the invention allows to maintain the enzyme or enzyme cluster in a natural confinement so that the three dimensional conformation of the enzyme active site and the enzyme activity are preserved.

An enzyme may function in synthesis and/or degradation, a catabolic reaction and/or an anabolic reaction, and other types of reversible reactions. For example, an enzyme normally described as an esterase may function as an ester synthetase depending upon the concentration of the substrate(s) ("reactants") and/or the product(s), such as an excess of hydrolyzed esters, typically considered the product of an esterase reaction, relative to unhydrolyzed esters, typically considered the substrate of the esterase reaction. In another example, a lipase may function as a lipid synthetase due to a relative abundance of free fatty acid(s) and alcohol moiety(s) to catalyze the synthesis of a fatty acid ester. Any reaction that an enzyme may be capable of is contemplated, such as, for example, a transesterification, an interesterification, and/or an intraesterification, and the like, being conducted by an esterase.

In the context of a biomolecule or macromolecule, "active" or "bioactive" refers to the effect of a biomolecule or macromolecule (such as conferring and/or altering a property) of a nanoencapsulation system according to the invention. For example, in the case of an enzyme, as used herein, the term "bioactive" or "active" refers to the ability of the enzyme to accelerate a chemical reaction differentiating such activity from a like ability of a composition, an article, a method, etc. that does not comprise an enzyme to accelerate a chemical reaction.

In exemplary embodiments, an enzyme may comprise a simple enzyme, a complex enzyme, or a combination thereof. As used herein, a "simple enzyme" comprises an enzyme wherein a chemical property of one or more moiety(s) found in its amino acid sequence produces enzymatic activity. As used herein, a "complex enzyme" comprises an enzyme whose catalytic activity functions when an apo-enzyme combines with a prosthetic group, a co-factor, or a combination thereof. An "apo-enzyme" comprises a proteinaceous molecule and may be relatively catalytically inactive without a prosthetic group and/or a co-factor. As used herein, a "prosthetic group" or "co-enzyme" comprises a non-proteinaceous molecule that may be attached to the apo-enzyme to produce a catalytically active complex enzyme. As used herein, a "holo-enzyme" comprises a complex enzyme comprising an apo-enzyme and a co-enzyme. As used herein, a "co-factor" comprises a molecule that acts in combination with the apo-enzyme to produce a catalytically active complex enzyme. In some aspects, a prosthetic group comprises one or more bound metal atoms, a vitamin derivative, or a combination thereof. Examples of a metal atom that may be used in a prosthetic group and/or a co-factor include Ca, Cd, Co, Cu, Fe, Mg, Mn, Ni, Zn, or a combination thereof. Usually the metal atom comprises an ion, such as $Ca^{2+}$, $Cd^{2+}$, $CO^{2+}$, $Cu^{2+}$, $Fe^{+2}$, $Mg^{2+}$, $Mn^{2+}$, $Ni^{2+}$, $Zn^{+2}$, or a combination thereof. As used herein, a "metalloenzyme" comprises a complex enzyme comprising an apo-enzyme and a prosthetic group, wherein the prosthetic group comprises a metal atom. As known herein, a "metal activated enzyme" comprises a complex enzyme comprising an apo-enzyme and a co-factor, wherein the co-factor comprises a metal atom.

As used herein the phrase "systemically delivering" refers to providing organs (internal or external) of the body via the blood circulation.

As used herein the phrase "recombinant biomolecule" refers to a polynucleotide, an oligonucleotide, a polypeptide or a peptide (such as a peptide fragment of a larger polypeptide) which is exogenously expressed (mRNA or protein level) using recombinant DNA technology.

Examples of proteins which may be recombinantly expressed include but are not limited to prokaryotic proteins, eukaryotic proteins (e.g., mammalian, plant), chimeric proteins, viral proteins and peptides. Specific examples include, but are not limited to, antibodies, hormones, growth factors, proteases, extra-cellualr matrix proteins (e.g., collagen), enzymes, the infectious bursal disease virus viral protein VPII, Human interferon beta, Human clotting factor, Human factor X, Human lysosomal enzyme, Human glucocerebrosidase, human alpha galactosidase, and Acetyl Choline esterase and high mannose proteins [e.g., Human Cox-2, Human EGF, Human uterine tissue plasminogen activator (tPA), Human DNase I, recombinant gp120, Human tissue plasminogen activator, Human thyroglobulin (hTG), Human CD4 and Human plasminogen)].

It will be appreciated that other biomolecules can be delivered using the teachings of the present invention such as oligonucleotides which are involved in gene silencing (e.g., antisense, dsRNA, ribozyme, DNAzyme and the likes).

As used herein, the expression "consists essentially of" or "consisting essentially of" means that additional components than those that are recited can be present, provided that the additional components, or the amounts of additional components, provided that the basic and novel characteristics of the invention are not materially affected. For example, as used herein, the term "consisting essentially of", with respect to the components of a nanoencapsulated bioactive macromolecule or bioactive macromolecule cluster composition, means the composition contains the recited components, and may contain additional components provided that the additional components do not alter the encapsulated bioactive macromolecule or bioactive macromolecule cluster's ability to carry out its intended biological function upon disintegration of the silica capsule shell. For example, as used herein, the term "consisting essentially of", with respect to the components of a nanoencapsulated bioactive macromolecule or bioactive macromolecule cluster composition, excludes surfactants capable of forming stable liposomes (typically surfactants whose packing parameter is between ½ to 1, like for example phospholipids (such as lecithin)) within hollow core of the nanocapsule.

DETAILED DESCRIPTION OF CERTAIN PREFERRED EMBODIMENTS OF THE INVENTION

The present invention encompasses methods and compositions for the administration of biologically active macromolecules which can be used for diagnostic, cosmetic, prophylactic or therapeutic purposes.

In this context, there is provided herein novel core/shell hybrid organosilica materials, for example in the form of nanoparticles/nanocapsules, whose shell framework contains Si adjacent sites covalently bound via a responsively cleavable linker.

1) General Description of Core/Shell Hybrid Organosilica Materials of the Invention In one aspect, there is provided a nanoencapsulated bioactive macromolecule or bioactive macromolecule cluster, consisting essentially of:
(a) a disintegratable nanocapsule having a core/shell structure, wherein the shell of said nanocapsule is made of hybrid organosilica material comprising a three-dimensional framework of Si—O bonds, wherein at least a subset of Si atoms in the material's framework are connected to at least another Si atom in the framework through a linker having the following structure:

*—R$^1$—L—R$^2$—*;

wherein:
each occurrence of * denotes a point of attachment to a Si atom in the material's framework;
L represents a responsively cleavable covalent bond, and R$^1$ and R$^2$ independently represent an optionally substituted C1-20alkylenyl moiety, an optionally substituted C1-20heteroalkylenyl moiety, an optionally substituted ethylenyl moiety, —C≡C— or an optionally substituted phenyl moiety, wherein the C1-20alkylenyl, C1-20heteroalkylenyl or ethylenyl moiety may bear one or more substituents selected from halogen or —OR where R may represent H or C1-6alkyl, and the phenyl moiety may bear one or more substituents independently selected from halogen, C1-6alkyl, —NO$_2$, —CN, isocyano, —OR$^P$, —N(R$^P$)$_2$ wherein each occurrence of R$^P$ independently represents H or C1-6alkyl; and
(b) a bioactive macromolecule or bioactive macromolecule cluster encapsulated within said nanocapsule.

Advantageously, the bioactive macromolecule or bioactive macromolecule cluster encapsulated within the nanocapsule is in active conformation (i.e., in a biologically active form).

Advantageously, the bioactive macromolecule or bioactive macromolecule cluster encapsulated within the nanocapsule is in undenatured state.

Advantageously, the bioactive macromolecule or bioactive macromolecule cluster encapsulated within the nanocapsule remains in a folded position and retains an active conformation.

Advantageously, the nanocapsule having a core/shell structure encapsulating the bioactive macromolecule or bioactive macromolecule cluster encapsulated within, does not encapsulate a micellar phase in its inner core. Advantageously, it does not encapsulate a phospholipid bilayer micellar phase.

Advantageously, the nanocapsule having a core/shell structure encapsulating the bioactive macromolecule or bioactive macromolecule cluster encapsulated within, does not encapsulate surfactants in its inner core. In particular, it does not encapsulate surfactants capable of forming stable liposomes, such as surfactants whose packing parameter (P) is between ½ to 1, where P is defined as:

$P = v/(a \cdot 1)$, where v represents the volume of the hydrocarbon portion of the surfactant molecule
a represents the effective area of the polar head group
l represents the length of the hydrocarbon chain of the surfactant molecule (e.g., the length of the lipid tail when the surfactant is a phospholipid).

Advantageously, the nanocapsule having a core/shell structure does not encapsulate a phospholipid together with the bio active macromolecule or bioactive macromolecule cluster, for example lecithin.

Advantageously, the amount of linker L within the hybrid organosilica material may be selected to effected a desired disintegration speed of the nanocapsule. This will be referred as the "% doping" of the hybrid organosilica material. For example, the hybrid organosilica material may be "at least 30% doped". As used herein, "x" in the expression "x % doped" is calculated based on the % of metal centers in the organosilica material that comes from the starting material (X)$_3$Si—R$^1$—L—R$^2$—Si(X)$_3$ used to synthesize the hybrid organosilica material nanocapsule according to the invention. This % doping also reflects the contents of responsively cleavable covalent bond L in the hybrid organosilica shell. The higher the % doping, the higher the content of linker L in the hybrid organosilica material, and the greater the ability of the resulting hybrid organosilica nanocapsule to undergo complete structural breakdown, suitable for the intended applications.

Advantageously, the subset of silicon atoms in the nanocapsule shell material's framework that are connected to the linker *—R1-L-R2-*, may range anywhere from 30% to 100% of the silicon atoms present in the hybrid organosilica material. For example, the subset of silicon atoms in the material's framework that are connected to the linker *—R1-L-R2-*, may range from 30% to 100%, from 30% to 90%, from 30% to 80%, from 30% to 70%, from 30% to 60%; from 30% to 50%, from 30% to 40%, of the silicon atoms present in the hybrid organosilica material of the invention. The final % doping of the hybrid organosilica material will depend on the respective molar ratios of starting materials (X)$_3$Si—R$^1$—L-R$^2$—Si(X)$_3$ and Si(X$^A$)$_4$ used in the synthesis of the material (cf. section dealing with synthetic process, later in the present document). When no Si(X$^A$)$_4$ is used in the preparation of the material, a doping of 100% will be reached (i.e., only (X)$_3$Si—R$^1$—L-R$^2$—Si(X)$_3$ is used as silicon source).

Advantageously, for a slower and more controlled desintagrability/degradability of the hybrid organosilica material, the subset of silicon atoms in the material's framework that are connected to the linker *—R1-L-R2-*, may be in the lower % range; for example from 30% to 35%, from 30% to 40%, from 30% to 45%, from 30% to 50%, of the silicon atoms present in the hybrid organosilica material of the nanocapsule shell. Advantageously, the subset of silicon atoms in the material's framework that are connected to the linker *—R1-L-R2-*, may range from 30% to 40%, preferably about 30%.

Advantageously, for a faster desintagrability/degradability of the hybrid organosilica material of the nanocapsule shell, the subset of silicon atoms in the material's framework that are connected to the linker *—R1-L-R2-*, may be in the higher % range; for example from 55% to 60%, from 55% to 65%, from 55% to 70%, from 55% to 75%, from 55% to 80%, from 55% to 85%, from 55% to 90%, from 55% to 95%, from 55% to 100%, of the silicon atoms present in the hybrid organosilica material of the nanocapsule shell.

Advantageously, in the linker *—R$^1$—L—R$^2$—*, each occurrence of R$^1$ and R$^2$ may be identical.

Advantageously, in the linker *—R$^1$—L—R$^2$—*, R$^1$ and R$^2$ may be any organic radical from any commercially available silylated derivative suitable for sol-gel chemistry. For example, R$^1$ and R$^2$ may independently represent —CH$_2$—, —(CH$_2$)$_2$—, —(CH$_2$)$_3$—, —(CH$_2$)$_4$—, or phenyl.

Advantageously, R$^1$ and R$^2$ may be identical and may each represent —CH$_2$—, —(CH$_2$)$_2$—, —(CH$_2$)$_3$—, —(CH$_2$)$_4$—, or phenyl.

Advantageously, the substituent(s) on R$^1$ and R$^2$ may be suitably selected to facilitate the cleavage of the responsively cleavable linker L when an external signal/stimulus is applied (e.g., a change in pH (either an increase or decrease), a change in redox potential, the presence of reduction or oxidation agent, the presence of UV light or near infrared light, an enzymatic cleavage, a change in temperature, etc.). For example, the substituent(s) on R$^1$ and R$^2$ may be selected based on their electron-withdrawing or—donating properties, to facilitate the cleavage of the linker moiety. For example, for illustrative purposes, when L may be an imine bond and $R_1$ and/or $R_2$ may be a phenyl group, the phenyl group may bear a nitro group to make the imine bond more reactive (i.e., more responsive to cleavage upon application of a suitable stimulus).

One advantageous aspect of this invention resides in the simple, yet compelling, underlying concept: namely a precursor having one the following structures:

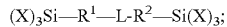

wherein L, $R^1$, and $R^2$ are as defined above, is chemically inserted within the framework of the hybrid organosilica nanocapsule shell via sol-gel chemistry. In the above, X may represent a hydrolysable or nonhydrolyzable group, provided that on each occurrence of Si, at least one occurrence of X represents a hydrolysable group.

When X represents a hydrolysable group, it may be selected from a C1-6 alkoxy, C1-6 acyloxy, halogen or amino moiety. Advantageously, when X represents a hydrolysable group, X may represent Cl, —OMe, —OEt, —OiPr or —OtBu.

When X represents a nonhydrolyzable group, it may be selected from an optionally substituted C1-20 alkyl, C2-20 alkenyl or C2-20 alkynyl moiety, an optionally substituted C1-20 heteroalkyl, C2-20 heteroalkynyl or C2-20 heteroalkynyl moiety, or an optionally substituted phenyl moiety, wherein the substituents on the phenyl, alkyl, alkenyl, alkynyl, heteroalkyl, heteroalkenyl and heteroalkynyl moieties may be independently selected from halogen, —NO$_2$, —CN, isocyano, C1-6 alkoxy, an oxirane/epoxyde moiety, —N(R)$_2$ wherein each occurrence of R is independently selected from H or C1-6 alkyl.

Advantageously, when X represents a nonhydrolyzable group, X may represent C1-6 alkyl or C2-6 alkenyl; preferably —Me, —Et or —CH═CH$_2$; most preferably —Me or —Et.

The insertion of the responsively cleavable linker within the framework of the hybrid organosilica nanocapsule shell is performed during the synthesis of the hybrid organosilica nanocapsule shell itself, no additional step is required, if not the preparation of the required (X)$_3$Si—R$^1$—L-R$^2$—Si(X)$_3$ precursor, which may also be carried out in situ. It is then important to choose the correct (X)$_3$M$_1$-R$^1$—L-R$^2$—M$_2$(X)$_3$ precursor in order to obtain the desired self-destructive behavior in the final operational environment.

Advantageously, the hybrid organosilica nanocapsule shell may be a hybrid material. The hybrid organic/inorganic nature of the shell is naturally conferred by the presence of the organic moiety *—R$^1$—L—R$^2$—*. However, other organic moieties may be introduced in the hybrid organosilica nanocapsule shell by conventional sol-gel chemistry methods known in the art. For example, the use of a R$^3$—Si(R$^4$)$_3$ precursor, wherein R$^3$ is a nonhydrolyzable organic moiety bound to Si via a carbon atom, and each occurrence of R$^4$ is independently a hydrolysable group. By "nonhydrolyzable organic moiety" is meant an organic moiety that is not cleaved from the metal Si during the sol-gel process leading to the hybrid organosilica nanocapsule shell. Conversely, by "hydrolyzable group" is meant a radical that is hydrolyzed (cleaved from the metal Si) during the sol-gel process leading to the hybrid organosilica nanocapsule shell. Typically, R$^4$ may be a C1-6 alkoxy, C1-6 acyloxy, halogen or amino group. R$^3$ may be an optionally substituted C1-20 alkyl, C2-20 alkenyl or C2-20 alkynyl moiety, an optionally substituted C1-20 heteroalkyl, C2-20 heteroalkynyl or C2-20 heteroalkynyl moiety, or an optionally substituted phenyl moiety. Advantageously, R$^3$ may bear a substituent that allows further functionalization of the hybrid organosilica nanocapsule shell, or posses a functionality that imparts desired characteristics. For example, the substituents on the phenyl, alkyl, alkenyl, alkynyl, heteroalkyl, heteroalkenyl and heteroalkynyl moieties may be independently selected from halogen, —NO$_2$, —CN, isocyano, C1-6 alkoxy, an oxirane/epoxyde moiety, —N(R)$_2$ wherein each occurrence of R is independently selected from H or C1-6alkyl. Organic/inorganic hybrid Si-based framework materials are well-known in the literature, as well as methods for their preparation. (See for example, J. Pyun, S. Jia, T. Kowalewski, G. D. Patterson, K. Matyjaszewski, Macromolecules, 2003, 36, 5094-5104; [3] C. Sanchez, B. Julian, P. Belleville, M. Popall, J. mater. Chem. 2005, 15, 3559-3592; [4] S. R. Hall, S. S. Davis, S. Mann, Langmuir, 2000, 16, 1454-1456 [5]; Inagaki, S.; Guan, S.; Ohsuna, T.; Terasaki, O. *Nature* 2002, 416, 304-307 [6]; Asefa, T.; MacLachlan, M. J.; Coombs, N.; Ozin, G. A. *Nature* 1999, 402, 867-871. [7] These methods may be readily adapted to the present hybrid organosilica nanocapsule shell, by using a (X)$_3$Si—R$^1$—L-R$^2$—Si(X)$_3$ precursor as defined above and herein, in the sol-gel synthetic process.

Advantageously, the hybrid organosilica nanocapsule shell may be in the form of nanoparticles. For example, the hybrid organosilica nanocapsule shell according to the invention may have a diameter from 1 to 999 nanometers, preferably from 1 to 500 nm, more preferably from 1 to 250 nm and most particularly from 1 to 100 nm. Advantageously, the hybrid organosilica nanocapsule shell according to the invention may have a diameter from 25 to 500 nm, preferably from 25 to 200 nm, preferably from 40 to 90 nm, preferably from 40 to 80 nm.

Advantageously, the hybrid organosilica nanocapsule shell may be in the form of nanoparticles dispersed in a solvent. The solvent may be that used in the synthesis of the material.

In yet another aspect, the present invention relates to the preparation of nanoparticulate systems for administering, among others, biologically active macromolecules.

In the present invention, the term "nanoparticles" or "nanocapsules" refers to stable structures having homogenous, reproducible and modulable characteristics that can be perfectly differentiated from self-assembled systems.

Advantageously, the nanoparticles of the system of the invention have an average particle size of less than 1 mm, i.e., they have an average size of between 1 and 999 nm, preferably of between 25 and 200 nm, most preferably between 40 and 80 nm. The average particle size is mainly influenced by the composition and the conditions for particle formation.

The term "average size" is understood as the average diameter of the nanoparticle population of the invention. The average size of these systems can be measured using standard methods known by the person skilled in the art.

In addition, the nanoparticles may have an electric charge (measured by means of the Z potential), the magnitude of which advantageously have negative values, which denotes that the outer surface of the particles is ade of silica and that the encapsulated bioactive macromolecules or macromolecule clusters do not protrude on the surface of the nanocapsule. In a particular embodiment of the invention, the nanoparticles have a negative charge ranging between −9.0 and −30.0 mV, preferably between −9.0 and −20.0 mV.

The zeta potential of the particle of the systems of the invention can be measured using standard methods known by the person skilled in the art which are described, for example, in the experimental part of the present specification.

Advantageously, the bioactive macromolecule may be selected from the group consisting of proteins, enzymes, oligonucleotides, antibodies, peptides, PNA, DNA, RNA, and gene fragments.

Proteins: fluorescence protein family such as GFP, RFP; Cytotoxic proteins such as: TRAIL/APO-2L, Onconase, Ricin, Parasporin; Therapeutic proteins: Insulin Family, Angiopoietin family, Coagulation factor proteins, Dystrophin, HIV antigen, Hepatitis C antigen.

Enzymes: RNAase, Hyaluronidase, Lysosomal enzyme acid alpha-glucosidase, Galactosidase, Glucocerebrosidase, Streptokinase, Urokinase, Altepase, Thymidine kinase, cytosine deaminase Oligonucleotides: DNA (Deoxyribonucleic acid), RNA (Ribo Nucleic acid), PNA (Peptide Nucleic acid), LNA (Locked Nucleic Acid)

Proteins for cosmetic: Botulinum toxin protein family, Elastin, Collagen, Keratin, Calcitonin, Silk proteins, Antibodies: Trastuzumab, Bevacizumab, Cetuximab, Mylotarg, Alemtuzumab, Rituximab, Brentuximab Other macromolecules: Sugars, polypeptide, Advantageously, L may be any moiety that contains a responsively cleavable covalent bond, which can be cleaved upon exposure to a determined stimulus. Advantageously, L may represent a responsively cleavable covalent bond selected from:

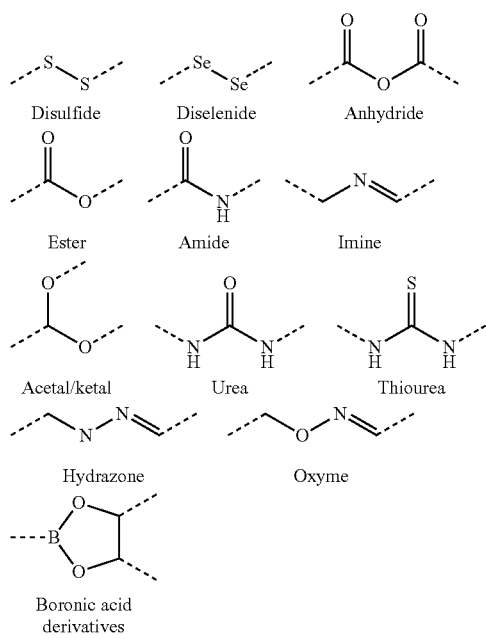

Preferably, L may represent a responsively cleavable covalent bond selected from disulfide, diselenides, imine, amide, ester, urea, or thiourea.

Advantageously, the cleavage/degradation of the linker *—$R^1$—L—$R^2$—* may be triggered by any suitable means. For example, it may be a change in pH (either an increase or a decrease), a change in redox potential, the presence of reduction or oxidation agent, application of UV, visible or near infrared light, ultrasounds, electromagnetic radiation, a change in temperature, enzymatic cleavage, DNA binding, etc. . . . . The following Table 1 gives examples of cleavage/degradation triggering means for each of the aforementioned types of responsively cleavable linkers:

TABLE 1

| L | Exemplary Triggers |
|---|---|
| Disulfide | Reducing agents (e.g., $NaBH_4$, dithiothreitol (DTT), glutathione) |
| Diselenide | Reducing agents (e.g. thiols, metal complexes) |
| Ester | pH, enzymatic cleavage (e.g. esterase) [8] |
| Amide | Enzymatic cleavage (e.g. amidase) [9] |
| Imine | pH |
| Acetal/ketal | pH |
| Anhydride | pH |
| Urea/thiourea | Enzymatic cleavage (e.g. urease) [10] |
| Hydrazone | pH |
| Oxyme | pH |
| Boronic acid (complexed with diols) | pH, sugars |
| Boronic esters | pH, reducing agents (e.g., $LiAlH_4$) |

2) Synthetic Overview:

In yet another aspect, there is provided a method for producing a new class of nanocomposite materials so called disintegratable hybrid organosilica core/shell nanocapsules. This new class of materials includes organometaloxide framework systems in whose framework a precursor having one of the following structures:

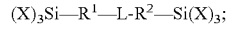

wherein L, $R^1$, and $R^2$ are as defined above, has been chemically inserted via conventional sol-gel chemistry.

Thus, in one aspect, there is provided a method of preparing nanoencapsulated bio active macromolecules by covalently introducing a preselected precursor (general structure $(X)_3Si$—$R^1$—L—$R^2$—$Si(X)_3$) with a responsively cleavable linker, as defined herein, in the framework of the material itself. As such, the resulting core/shell nanocapsules present controlled self-destructive behavior in the environment where it is intended to perform its activity. The controlled self-destructive behavior is a property that provides numerous avenues of important applications for such core/shell systems, ranging from medical to cosmetics.

The practitioner has a well-established literature of organometaloxide materials chemistry to draw upon, in combination with the information contained herein, for guidance on synthetic strategies, protecting groups, and other materials and methods useful for the synthesis of the disintegratable materials of this invention.

General Synthetic Methods

Advantageously, the method may comprise steps of:
a) Producing a water-in-oil emulsion from (i) a solution of a suitable surfactant and alcohol in a suitable organic solvent, and (ii) an aqueous solution of a bioactive macromolecule or bioactive macromolecule clusters, a silane precursor $Si(X^4)_4$ and a selected precursor having the structure $(X)_3Si$—$R^1$—L—$R^2$—$Si(X)_3$;
b) Stirring the water-in-oil emulsion obtained in step a) under alkaline conditions; thereby coating the bio active macromolecule or bioactive macromolecule clusters with an organosilica sol-gel mixture obtained by hydrolysis-condensation of silicon alkoxide; and
c) Adding a suitable organic solvent, thereby precipitating the nanoencapsulated bio active macromolecules or bioactive macromolecule clusters:

wherein:
each occurrence of X and $X^4$ independently represents a hydrolysable or nonhydrolyzable group, provided that on each occurrence of Si of the precursor $(X)_3Si$—$R^1$—L-$R^2$—$Si(X)_3$, at least one occurrence of X represents a hydrolysable group, and at least two occurrences of $X^A$ in the the precursor $Si(X^A)_4$ independently represent a hydrolysable group; wherein (i) when X or $X^A$ represents a nonhydrolyzable group, it may be selected from an optionally substituted C1-20alkyl, C2-20alkenyl or C2-20alkynyl moiety, an optionally substituted C1-20heteroalkyl, C2-20heteroalkynyl or C2-20heteroalkynyl moiety, or an optionally substituted phenyl moiety, wherein the substituents on the phenyl, alkyl, alkenyl, alkynyl, heteroalkyl, heteroalkenyl and heteroalkynyl moieties may be independently selected from halogen, —$NO_2$, —CN, isocyano, C1-6alkoxy, an oxirane/epoxyde moiety, —$N(R)_2$ wherein each occurrence of R is independently selected from H or C1-6alkyl; and (ii) when X or $X^A$ represents a hydrolysable group, it may be selected from a C1-6alkoxy, C1-6acyloxy, halogen or amino moiety;

L represents a responsively cleavable covalent bond; and $R^1$ and $R^2$ independently represent an optionally substituted C1-20alkylenyl moiety, an optionally substituted C1-20heteroalkylenyl moiety, an optionally substituted ethylenyl moiety, —C≡C— or an optionally substituted phenyl moiety, wherein the C1-20alkylenyl, C1-20heteroalkylenyl or ethylenyl moiety may bear one or more substituents selected from halogen or —OR where R may represent H or C1-6alkyl, and the phenyl moiety may bear one or more substituents independently selected from halogen, C1-6alkyl, —$NO_2$, —CN, isocyano, —$OR^P$, —$N(R^P)_2$ wherein each occurrence of $R^P$ independently represents H or C1-6alkyl.

Advantageously, in step c), the nanoencapsulated bioactive macromolecules or bioactive macromolecule clusters that precipitates out are encapsulated in disintegratable hybrid organosilica core/shell nanoparticles according to the present invention, wherein the bioactive macromolecule(s) within the nanocapsule is/are in an active conformation (i.e., in a biologically active form). Advantageously, the bioactive macromolecule or bioactive macromolecule cluster encapsulated within the nanocapsule is in undenatured state. Advantageously, the bioactive macromolecule or bioactive macromolecule cluster encapsulated within the nanocapsule remains in a folded position and retains an active conformation.

Advantageously, the nanocapsule does not encapsulate a micellar phase in its inner core. Advantageously, it does not encapsulate a phospholipid bilayer micellar phase.

Figure 24:
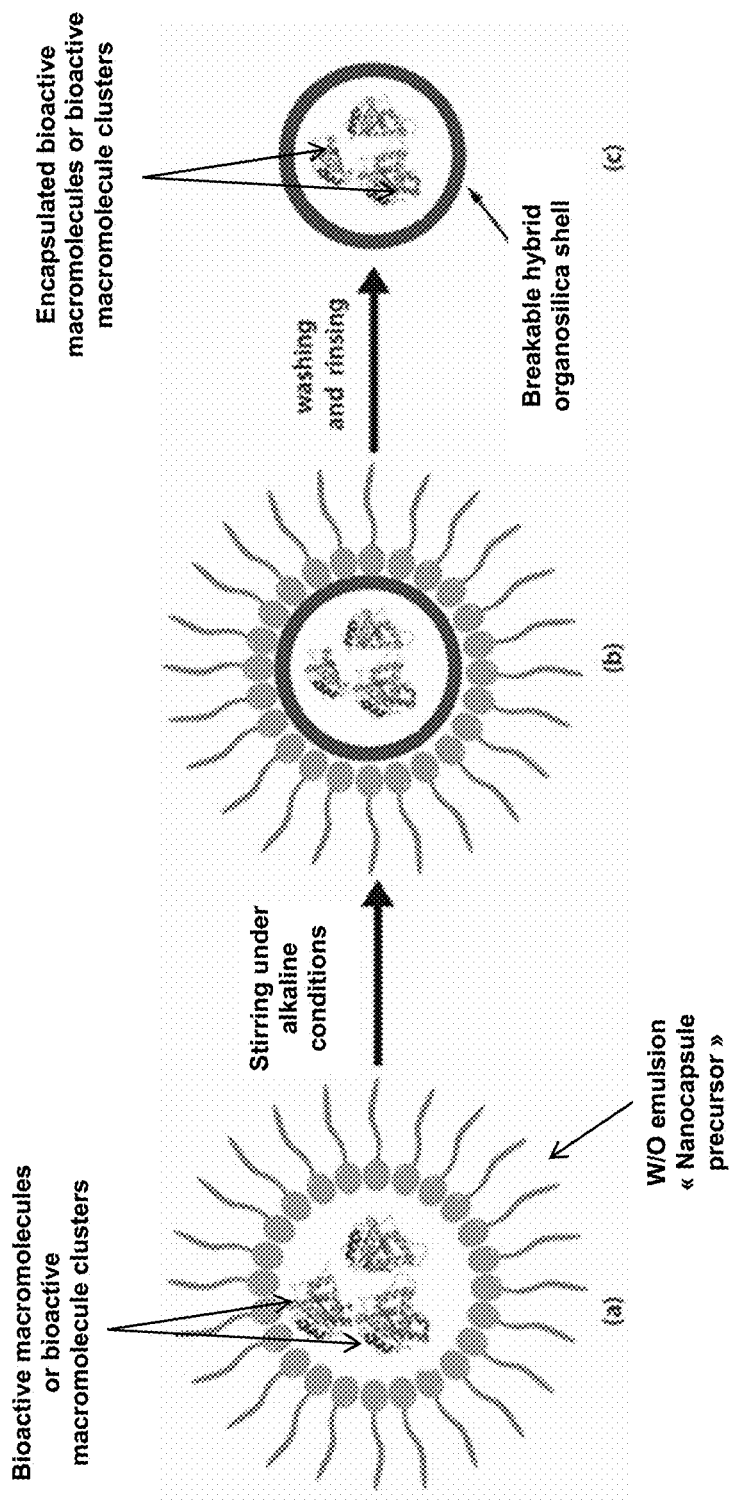
FIG. 24 schematically illustrates the process of encapsulation of bioactive macromolecule or bioactive macromolecule clusters according to an exemplary embodiment of the invention.

Without wishing to be bound by any particular theory, it is proposed that in step a), the surfactant forms micelles, which act as "nanoreactors" encapsulating the bioactive macromolecule or bioactive macromolecule clusters and get eventually coated with the hybrid organosilica shell in step b). The micelles formed in step a) essentially form a "nanocapsule precursor", which forms a spherical wall/template on the inner surface of which the disintegratable organosilica shell forms in step b). Thus, at the end of the process (after step c), the surfactant micelles are dispersed, leaving instead a disintegratable organosilica shell fully encapsulating the bioactive macromolecule or bioactive macromolecule clusters. See FIG. 24.

Advantageously, the aqueous medium used in step a) to prepare the aqueous solution of a bioactive macromolecule or bioactive macromolecule clusters may be any suitable aqueous medium in which the bioactive macromolecule or bioactive macromolecule clusters remain in a folded position, in an undenatured state, and retains an active conformation.

Advantageously, a minimum of 30% molar ratio (based on the silicon centers) of $(X)_3Si$—$R^1$—L-$R^2$—$Si(X)_3$ to 70% of $Si(X^A)_4$ precursor may be used. Because $(X)_3Si$—$R^1$—L-$R^2$—$Si(X)_3$ is bivalent (i.e., because this precursor contains two metal atoms per cleavable bond L), the ratio 0.15 eq $(X)_3Si$—$R^1$—L-$R^2$—$Si(X)_3$/0.70 eq $Si(X^A)_4$ means that the Si atoms from $(X)_3Si$—$R^1$—L-$R^2$—$Si(X)_3$ will represent 30% of the metal centers in the resulting hybrid organosilica nanocapsule shell material (i.e., 30% doping). For a doping of 100%, $(X)_3Si$—$R^1$—L-$R^2$—$Si(X)_3$ may be used as the only source of silicon (i.e., no $Si(X^A)_4$ is used). For exemplary ratios of equivalents $(X)_3Si$—$R^1$—L-$R^2$—$Si(X)_3$/$Si(X^A)_4$ to reach a variety of % doping ≥30%, see Table 1A.

The following Table 1A describes exemplary ratios of equivalents $(X)_3Si$—$R^1$—L-$R^2$—$Si(X)_3$/$Si(X^A)_4$ to reach the desired % doping (which is at least 30%):

TABLE 1A

| $Si(X^A)_4$ | $(X)_3Si$—$R^1$—L—$R^2$—$Si(X)_3$ | $(X)_3Si$—$R^1$—L—$R^2$—$Si(X)_3$ | % doping |
|---|---|---|---|
| 0.70 eq. | 0.30 eq.‡ | 0.15 eq.‡‡ | 30% |
| 0.60 eq. | 0.40 eq.‡ | 0.20 eq.‡‡ | 40% |
| 0.50 eq. | 0.50 eq.‡ | 0.25 eq.‡‡ | 50% |
| 0.40 eq. | 0.60 eq.‡ | 0.30 eq.‡‡ | 60% |
| 0.30 eq. | 0.70 eq.‡ | 0.35 eq.‡‡ | 70% |
| 0.20 eq. | 0.80 eq.‡ | 0.40 eq.‡‡ | 80% |
| 0.10 eq. | 0.90 eq.‡ | 0.45 eq.‡‡ | 90% |
| — | 1 eq.‡ | 0.5 eq.‡‡ | 100% |

‡equivalents expressed in terms of silicon atoms introduced by the bivalent starting material $(X)_3Si$—$R^1$—L—$R^2$—$Si(X)_3$ in the final hybrid organosilica material making up the nanocapsule shell.
‡‡equivalents expressed in terms of responsively cleavable bond L introduced by the bivalent starting material $(X)_3Si$—$R^1$—L—$R^2$—$Si(X)_3$ in the final hybrid organosilica material making up the nanocapsule shell.

The reaction conditions may be modulated, depending on the eq. ratios $(X)_3Si$—$R^1$—L-$R^2$—$Si(X)_3$/$Si(X^A)_4$ used. From the general knowledge in the field of organometaloxide chemistry, the practitioner will readily know how to adjust suitable reaction conditions, for example the type of solvent used to effect the reaction depending on the respective solubilities of the selected $(X)_3Si$—$R^1$—L-$R^2$—$Si(X)_3$ and $Si(X^A)_4$.

In an effort to avoid unnecessary repetitions, and for concision purposes, every single variant and embodiments described above in section 1) with respect to variables R1, R2, L, X, the precursor $(X)_3Si$—$R^1$—L-$R^2$—$SiX)_3$; % doping; as well as the linkers *—$R^1$—L—$R^2$—*, are applicable mutatis mutandis to the synthetic method described immediately above.

It will be appreciated that the exemplary responsively cleavable linkers described herein are for purposes of illustrating and are not in any way meant to limit the scope of the present invention. Other responsively cleavable linkers based on the same concept may also be used. The reader will know how to adapt the teachings described herein, and the Examples for suitable synthetic approaches for these other linkers.

Advantageously, in step b) a pH adjusting agent may be used to modulate the pH to the desired value. As the pH-adjusting agent, there can be mentioned, for example, acids such as sulfuric acid, hydrochloric acid and the like; and alkalis such as sodium hydroxide, ammonia and the like. Advantageously, in the case of disintegratable hybrid organosilica nanocapsules according to the present invention, the pH of the reaction system may be preferably adjusted to 0 to 5, most preferably 1 to 5, when an acid agent is used, and to 8 to 14, most preferably, 8 to 13, when an alkaline agent is used.

The resulting nanocapsule systems are hence able to respond to a specific trigger (e.g., chemical, physical or enzymatic stimulation), by undergoing a structural breakdown. This property leads to an improved material with bioactive macromolecule stabilization/protection ability, which confers the nanocapsule systems with great potential for a variety of applications including medical diagnostics, bioremediation, environmental clean-up, biocatalysis, and protein delivery, to name a few. Indeed, the unusual behavior of the nanocapsule systems according to the invention confers them an enhanced biodegradability, reducing larger particles into smaller, more easily hydrolysable, and consequently less harmful fragments. This in turn reduces the persistence phenomenon of the materials in their working environment, consequently reducing accumulation risks, and purification/removal costs. In addition, their enhanced disintegratability allows for controlled release of their contents (bioactive macromolecule) at the desired site of delivery.

Advantageously, $Si(X^4)_4$ may represent any Si source suitable for carrying out sol-gel organosilica framework synthesis, for example, colloidal silica, sodium silicate, silicon alkoxides, tetramethylammonium silicate and tetraethylorthosilicate (TEOS) and the like. Advantageously, $M(X^4)_4$ may represent a tetraalkoxysilanes such as tetramethoxysilane, tetraethoxysilane and tetrapropoxysilane, preferably tetraethoxysilane (TEOS).

Advantageously, the silane precursor $Si(X^4)_4$ may preferably contain an alkoxysilane having an organic functional group; in other word, at least one occurrence of $X^4$ may by substituted with a substituent bearing an organic functional group, such that it allows further functionalization. Using the alkoxysilane, it is possible to form a silica framework out of alkoxysilyl groups while disposing organic functional groups on the surfaces of the materials. It is further possible to give suitable properties to the disintegratable core/shell silica particles by chemically modifying the organic functional group with other organic molecules or the like.

Functionalized organosilane chemistry is well known, and the reader may refer to the following citations for illustrative synthetic guidance that may be readily adapted in the context of the present invention. [2]

Advantageously, the surfactant may be a cationic surfactant, an anionic surfactant, a non-ionic surfactant; preferably a nonionic surfactant such as a surfactant that has a hydrophilic polyethylene oxide chain and an aromatic or linear hydrocarbon liphophilic, diblock or triblock copolymer from polyethylene oxide and polypropylene oxide, preferably a nonionic surfactant such as Triton®, Brij®, Pluronic®.

Advantageously, the surfactant is such that it is not capable of forming stable liposomes. Preferably, the surfactant may have a packing parameter (P) outside the range ½ to 1. Advantageously, phospholipids, such as lecithin, are excluded as surfactants useable in the context of the present invention.

Because certain silane precursors $Si(X^4)_4$ like TEOS are not soluble in water alone, a co-solvent, preferably ethanol, may be added. Other solvent such as methanol or DMF can be used. Advantageously, the solvent system comprises an alcohol, such as methanol, ethanol, propanol, isopropanol, n-butanol, tert-butanol, hexanol and the like. Advantageously, the solvent system comprises hexanol due to its medium size aliphatic chain and thus its amphiphilic nature.

The thickness of the core/shell silica nanocapsules may be controlled by varying the type, the quantity and concentration of silica precursor and organosilica precursor, by controlling reaction temperature, and by adjusting the reaction time.

The mixing ratio of the silica precursors $Si(X^4)_4$ and $(X)_3Si—R^1—L-R^2—Si(X)_3$ to the surfactant is not particularly limited, but a molar ratio of 3:1 is preferred.

Advantageously, the linker may comprise a disulfide bond (—S—S—), a peptide bond, or an imine bond (—N=CH—), as responsively cleavable bond or moiety.

Advantageously, the precursor having the structure $(X)_3Si—R^1—L-R^2—Si(X)_3$ may be produced in situ. For example, a general synthetic approach for in situ generation of the precursor is depicted in Scheme 1 below:

TABLE 2

Exemplary synthetic conditions for preparing core/shell hybrid organosilica nanocapsules according to the invention

| Exemplary Sol-gel conditions | Responsively cleavable linker | Exemplary strategy | Exemplary starting materials |
|---|---|---|---|
| Suitable surfactant, TEOS, auxiliary solvent (e.g., EtOH, DMF, etc.) $(X)_3Si-R^1-L-R^2-Si(X)_3$ | L = —S—S— | Commercially available linker. |  |
| Suitable surfactant, TEOS, auxiliary solvent (e.g., EtOH, DMF, etc.) $(X)_3M_1-R^1-L-R^2-M_2(X)_3$ | L = —Se—Se— | Synthesis of a diselenide functionalized with 2 functional groups (e.g. double bonds) reactable with a silane source (e.g. $HSi(OEt)_3$). |  |
| Suitable surfactant, TEOS, auxiliary solvent (e.g., EtOH, DMF, etc.) $(X)_3Si-R^1-L-R^2-Si(X)_3$ | L = —C(=O)O— | Synthesis of an ester functionalized with 2 functional groups (e.g. double bonds) reactable with a silane source (e.g. $HSi(OEt)_3$). |  |
| Suitable surfactant, TEOS, auxiliary solvent (e.g., EtOH, DMF, etc.) $(X)_3Si-R^1-L-R^2-Si(X)_3$ | L = —C(=O)NH— | Bis-carboxylic acid molecule derivatized with a silane source (e.g. APTES). |  |

TABLE 2-continued

Exemplary synthetic conditions for preparing core/shell hybrid organosilica nanocapsules according to the invention

| Exemplary Sol-gel conditions | Responsively cleavable linker | Exemplary strategy | Exemplary starting materials |
|---|---|---|---|
| Suitable surfactant, TEOS, auxiliary solvent (e.g., EtOH, DMF, etc.) $(X)_3Si-R^1-L-R^2-Si(X)_3$ | L = —N=CH— | Condensation of an aldehyde (e.g. 4-(triethoxysilyl)butanal) and an amino-derivatized silane (APTES). |  |
| Suitable surfactant, TEOS, auxiliary solvent (e.g., EtOH, DMF, etc.) $(X)_3Si-R^1-L-R^2-Si(X)_3$ | L = -Acetal/ketal | Synthesis of acetals functionalized with 2 functional groups (e.g. double bonds) reactable with a silane source (e.g. HSi(OEt)₃). | 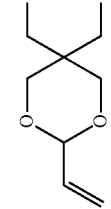 |
| Suitable surfactant, TEOS, auxiliary solvent (e.g., EtOH, DMF, etc.) $(X)_3Si-R^1-L-R^2-Si(X)_3$ | L = -Anhydride | Synthesis of an anhydride functionalized with 2 functional groups (e.g. double bonds) reactable with a silane source (e.g. HSi(OEt)₃). | 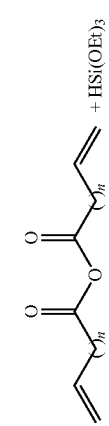 |
| Suitable surfactant, TEOS, auxiliary solvent (e.g., EtOH, DMF, etc.) $(X)_3Si-R^1-L-R^2-Si(X)_3$ | L = -Urea/thiourea | Condensation of an isocyanate (e.g. 3-(Triethoxysilyl)-propylisocyanate) and an amino-derivatized silane (e.g. APTES). | 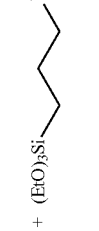 |
| Suitable surfactant, TEOS, auxiliary solvent (e.g., EtOH, DMF, etc.) $(X)_3Si-R^1-L-R^2-Si(X)_3$ | L = —N=N=CH— | Functionalization of an hydrazone with a silane derivative (e.g. 3-(triethoxysilyl)-propyl isocyanate). | 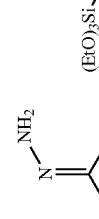 |
| Suitable surfactant, TEOS, auxiliary solvent (e.g., EtOH, DMF, etc.) $(X)_3Si-R^1-L-R^2-Si(X)_3$ | L = —O—N=CH— | Functionalization of an oxyme with a silane derivative (e.g. 3-(triethoxysilyl)-propyl chloride). |  |
| Suitable surfactant, TEOS, auxiliary solvent (e.g., EtOH, DMF, etc.) $(X)_3Si-R^1-L-R^2-Si(X)_3$ | L = -Boronic acid derivatives | Complexation with a tetraalcohol (i.e pentaerithritol) of a boronic acid possessing with 2 functional groups (e.g. double bonds) reactable with a silane source (e.g. HSi(OEt)₃). | 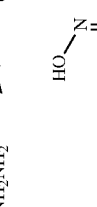 |

Scheme 1: Exemplary synthesis of a pH responsive linker

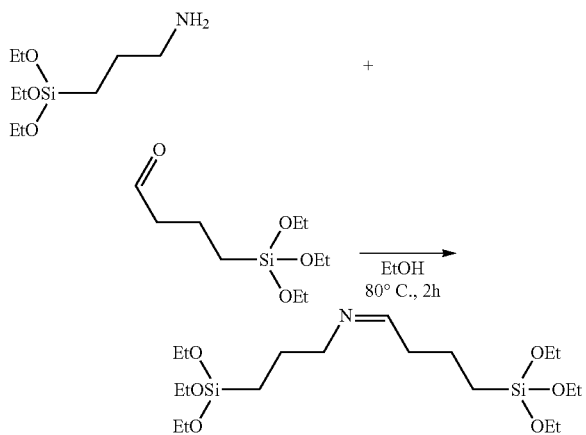

Advantageously, the surface of the core/shell silica nanocapsules according to the invention may be functionalized with a surface agent, for example by using a function group-containing trialkoxysilane, such as a PEG group linked to a trialkoxysilane. Likewise, marking of the core/shell silica nanocapsules (for example for medical purposes) may be achieved by condensation of a marker-containing trialkoxysilane. The marker may be selected from a contrast agent, a tracer, a radioactive marker, any commercial dye, such as a fluorescent marker or a phosphorescent marker, a magnetic resonance imaging agent or a positron emission tomography agent, such as pyrene, rhodamine, IR783, Gd-EDTA or $^{64}$Cu-EDTA. The marker may be a fluorescent molecule selected from rhodamines, fluorescein, luciferase, pyrene-containing markers, aminopyrrolidino-7-nitrobenzofurazan, or indocyanine green (ICG) for NIR emission.

As used herein, the term "surface agent" refers to a molecule that partly or totally covers the outer surface of the silica shell, allowing the surface properties of the material to be modified, for example:
- modifying its biodistribution, for example to avoid its recognition by the reticulo-endothelial system ("furtiveness"), and/or
- giving it advantageous bioadhesion properties during oral, ocular or nasal administration, and/or
- enabling it to specifically target certain sick organs/tissues, etc.

According to the invention, several surface agents may be used to combine the abovementioned properties. For example, a surface agent combining at least two of the abovementioned properties may be used. For example, the organic surface agent may be chosen from:
- an oligosaccharide, for instance cyclodextrins,
- a polysaccharide, for instance chitosan, dextran, fucoidan, alginate, pectin, amylose, starch, cellulose or xylan,
- a glycosaminoglycan, for instance hyaluronic acid or heparin,
- a polymer, for instance polyethylene glycol (PEG), polyvinyl alcohol or polyethyleneimine, or a polypeptide,
- a surface active agent, such as pluronic or lecithin,
- vitamins, such as biotin,
- coenzymes, such as lipoic acid,
- antibodies or antibody fragments,
- amino acids or peptides.

3) Compositions and Uses

The core/shell silica nanocapsules of the invention are useful for any application where controlled release of a bioactive macromolecule is desired. The core/shell silica nanocapsules of the invention are particularly adapted for uses of this type of materials where the self-destructive behavior that characterizes the core/shell silica nanocapsules of the invention provides an advantage, and for applications where preservation of the biological activity of the biomacromolecule is needed.

In particular, in contrast to conventional organometaloxide framework materials known in the art, the core/shell silica nanocapsules of the invention have the unexpected property of completely losing their structural integrity (disintegration) upon application of a suitable stimuli. Owing to their disintegratable properties, the core/shell silica nanocapsules of the invention prove much more efficient in releasing and delivering macromolecules that they encapsulate (e.g., therapeutically and/or cosmetically active macromolecular principles). In other words, release of the macromolecules trapped/encapsulated in the core/shell silica nanocapsules occurs much more efficiently than with conventional organometaloxides known in the art. For biomedical applications (e.g., when the framework metal is Si), this means less bio-accumulation, better elimination, and less toxicity.

Accordingly, there is provided compositions comprising a nanoencapsulated bioactive macromolecule according to the invention and any compound and/or additive suitable for any one or more of the material's intended use describe above.

For example, there is provided a pharmaceutical composition comprising nanoencapsulated bioactive macromolecule according to the invention, and a pharmaceutically acceptable carrier, adjuvant or vehicle. In exemplary embodiments, these compositions optionally further comprise one or more additional therapeutic agents.

In another example, there is provided a cosmetic composition comprising nanoencapsulated bioactive macromolecule according to the invention, and a cosmetically acceptable carrier, adjuvant or vehicle. In certain embodiments, these compositions optionally further comprise one or more additional cosmetically useful agents.

In another aspect, there is provided a nanoencapsulated bioactive macromolecule or bioactive macromolecule cluster according to the invention, for use as medicament.

In another aspect, there is provided a nanoencapsulated bioactive macromolecule or bioactive macromolecule cluster according to the invention, in a cosmetic composition.

In another aspect, there is provided a nanoencapsulated bioactive macromolecule or bioactive macromolecule cluster according to the invention, for delivering a cosmetically bioactive macromolecule to the skin. In exemplary embodiments, the cosmetically bioactive macromolecule is collagen, keratin, elastin, calcitonin or silk proteins.

In another aspect, there is provided a method for systemically delivering a bioactive macromolecule, in a biologically active form, to a subject in need thereof, the method comprising, administering to the subject a therapeutically effective amount of a nanoencapsulated bioactive macromolecule or bioactive macromolecule cluster according to the invention. In exemplary embodiments, the bioactive macromolecule is selected from the group consisting of a hormone, a growth factor, a protease, an extra-cellular matrix protein, an enzyme, an infectious viral protein, an antisense oligonucleotide, a dsRNA, a ribozyme and a DNAzyme. In exemplary embodiments, the bioactive macromolecule is an enzyme and said biological activity is a catalytic activity. In exemplary embodiments, the bioactive macromolecule is a hormone and said biological activity is a ligand binding activity.

In another aspect, there is provided a unit dosage form for local delivery of a bioactive macromolecule to a tissue of a subject, the unit dosage form comprising, a therapeutically effective amount of a nanoencapsulated bioactive macromolecule or bioactive macromolecule cluster according to the invention. In exemplary embodiments, the macromolecule is selected from the group consisting of a hormone, a growth factor, a protease, an extra-cellular matrix protein, an enzyme, an infectious viral protein, an antisense oligonucleotide, a dsRNA, a ribozyme and a DNAzyme.

In another aspect, there is provided a method for treating a disease in a subject-in-need thereof, the method comprising administering to the subject a. therapeutically effective amount of a nanoencapsulated bioactive macromolecule or bioactive macromolecule cluster according to the invention, thereby treating the disease in the subject.

In another aspect, there is provided a delivery system for enhancing the circulation time of a bioactive macromolecule of therapeutic interest in vivo, said system comprising a nanoencapsulated bioactive macromolecule or bioactive macromolecule cluster according to the invention; wherein the thickness of the nanocapsule shell is being adaptable to deliver the encapsulated bioactive macromolecule of therapeutic interest into in vivo circulation at a controlled rate of release.

In another aspect, there is provided a nanoencapsulation system and nanocapsules, and a method of using these encapsulation systems to enhance protein/enzyme reactivity.

In another aspect, there is provided the use of disintegratable silica core/shell nanocapsules according to the invention to protect proteins and enzymes from inactivation in a variety of harsh environments such as extreme pH.

In another aspect, there is provided a method of using disintegratable silica core/shell nanocapsules according to the invention as controlled-release agents or carriers for macromolecular drug, protein, and vaccine delivery.

The disintegratable hybrid organosilica core/shell materials according to the invention therefore can find applications in in vitro and in vivo diagnostics, therapy, in cosmetics, in drug delivery, and in any other application where a release can be envisaged.

Other advantages may also emerge to those skilled in the art upon reading the examples below, with reference to the attached figures, which are provided as nonlimiting illustrations.

EQUIVALENTS

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

EXEMPLIFICATION

The core/shell particles of this invention and their preparation can be understood further by the examples that illustrate some of the processes by which these particles are prepared or used. It will be appreciated, however, that these examples do not limit the invention. Variations of the invention, now known or further developed, are considered to fall within the scope of the present invention as described herein and as hereinafter claimed.

The present invention will now be exemplified using hybrid silica shell as responsively disintegratable protective shell for certain proteins but it will be understood this is not meant to limit the invention.

The tested core-shell system will be tested in their triggered shell disintegratability, and evidence of the breakdown of the shell will be given by demonstrating the structural/morphological transformations occurring in the responsively disintegratable shell during the triggered disintegration process.

In the Examples that follow, in the nomenclature "XX@BS-NP", "XX" represents the name/identity of the bioactive macromolecule, "BS" signifies "breakable shell" or "disintegratable shell" within the meaning of the present invention and "NP" signifies "nanoparticles". Likewise, in the nomenclature "XX@nonBS-NP", "XX" represents the name/identity of the bioactive macromolecule, "nonBS" signifies "non-breakable shell" or "non-disintegratable shell" (i.e., silica shell without responsively cleavable linker according to the invention incorporated within the Si-based framework, and "NP" signifies "nanoparticles".

Example 1—Construction of Disintegratable Silica Shell for Encapsulation of Cytochrome C Protein from Equine Heart (CyC@BS-NP)

Synthesis

Triton X-100 (1.77 mL) and n-hexanol (1.8 mL) were dissolved in Cyclohexane (7.5 mL). Separately, 300 µL of a 2.5 mg/mL aqueous solution of Cytochrome C from equine heart were mixed with 40 µL of tetraethyl orthosilicate (TEOS) and 60 µL of bis[3-(triethoxysilyl)propyl]disulfide. After shaking, this mixture was added to the previous organic mixture. Finally, 50 µL of 30% Ammonia aqueous solution were added and the water-oil emulsion was stirred overnight at room temperature.

After that, 20 mL of pure acetone were added in order to precipitate the CyC@BS-NP particles and the material was recovered by means of centrifugation, washing with ethanol 3 times.

If not otherwise needed, the particles were stored as a dispersion in water at 4° C.

Variation of Disulfide Bridge Content

It is possible to carry out the same synthetic procedure by changing the ratio between TEOS and bis[3-(triethoxysilyl)propyl]disulfide to different values, i.e. 70/30, 50/50, 40/60 µL/µL, to get particles containing a different percentage of disulfide bridges. SEM characterization showed the different ratios did not affect the sizes and shapes of the final particles obtained in the different conditions.

Chemical Biodegradability Test and Simulation of Protein Delivery

Reduction of the S—S bond was performed with Sodium Borohydride ($NaBH_4$), being an efficient and irreversible reducing agent, not forming residual by-products, which may interfere in the evaluation of the efficacy of the reduction. $NaBH_4$ (2 mg) was added to 1 mL of a 0.5 mg/mL dispersion in water of the CyC@BS-NP nanoparticles. The mixture was stirred overnight at room temperature. After that, the sample was centrifuged and the supernatant was recovered to be analyzed through UV-Vis spectroscopy, to check out the presence of the delivered protein.

Reduction of the S—S bond was also performed with Glutathione mimicking the process inside of the living cell. Glutathione (5 mM) was added to 1 mL of a 0.5 mg/mL dispersion in water of the CyC@BS-NP nanoparticles. The mixture was stirred overnight at room temperature. After that, the sample was centrifuged and the supernatant was recovered to be analyzed through UV-Vis spectroscopy, to check out the presence of the delivered protein.

Cellular Uptake Study:

Approximately 50,000 HeLa cells were grown on 24 well plates overnight. The media were removed and replaced with 0.05 mg/ml of cy5 functionalized CyC@BS-NP dispersion. The cells were incubated for 24 hours at 37° C. under a 5% $CO_2$ atmosphere. After the incubation, the media were removed and the cells were gently washed with PBS twice. Cells were fixed with 4% paraformaldehyde (PFA) and, subsequently, the cell nuclei were stained with DAPI (4',6-Diamidino-2-Phenylindole) and the F-actins were stained by Alexa Fluor® 568 Phalloidin. After staining, cells were washed once with PBS and then with water. Cells were removed from the well and mounted onto the rectangular glass cover for confocal microscopy experiments.

Cellular Uptake and Cytotoxicity Study

Cell viability was measured by an automatic cell counter CASY (Roche Innovatis AG, Bielefeld, Germany). 50,000 C6 Glioma cells were grown in 2 ml of culture media inside 6 well plates at 37° C., 5% $CO_2$ environment for 24 hours. Culture media were removed and replaced by dispersion containing 0.2 mg/ml of CyC@BS-NP, followed by cell incubation. After 24 hours of incubation, the culture media were removed to an eppendorf tube and 0.5 ml of trypsin were added. In order to detach the cell from the surface of the plate, cells were incubated for the next 5 minutes. Subsequently, 1.5 ml of new culture media were added to neutralize trypsin. Cell suspension together with first solution collected were removed into 10 ml eppendorf tube and centrifuged at 1000 rpm for 5 minutes. Supernatant were removed and cell palates were suspended into 1 ml of new culture media. 100 µl of the cell suspension was dissolved in 10 ml of CASYton solution and measurement was performed.

Example 2—Construction of NON-Disintegratable Silica Shell for Encapsulation of Cytochrome C Protein from Equine Heart (CyC@NonBS-NP)

Synthesis

Triton X-100 (1.77 mL) and n-hexanol (1.8 mL) were dissolved in Cyclohexane (7.5 mL). Separately, 300 µL of a 2.5 mg/mL aqueous solution of Cytochrome C from equine heart were mixed with 100 µL of tetraethyl orthosilicate (TEOS). After shaking, this mixture was added to the previous organic mixture. Finally, 50 µL of 30% Ammonia aqueous solution were added and the water-oil emulsion was stirred overnight at room temperature.

After that, 20 mL of pure acetone were added in order to precipitate the CyC@NonBS-NP particles and the material was recovered by means of centrifugation, washing with ethanol 3 times.

If not otherwise needed, the particles were stored as a dispersion in water at 4° C.

Chemical Biodegradability Test and Simulation of Protein Delivery

Chemical biodegradability of the shell was performed with Glutathione mimicking the process inside of the living cell. Glutathione (5 mM) was added to 1 mL of a 0.5 mg/mL dispersion in water of the CyC@NonBS-NP nanoparticles. The mixture was stirred overnight at room temperature. After that, the sample was centrifuged and the supernatant was recovered to be analyzed through UV-Vis spectroscopy, to check out the presence of the delivered protein.

Cellular Uptake and Cytotoxicity Study

Cell viability was measured by an automatic cell counter CASY (Roche Innovatis AG, Bielefeld, Germany). 50,000 C6 Glioma cells were grown in 2 ml of culture media inside 6 well plates at 37° C., 5% $CO_2$ environment for 24 hours. Culture media were removed and replaced by dispersion containing 0.2 mg/ml of CyC@NonBS-NP, followed by cell incubation. After 24 hours of incubation, the culture media were removed to an eppendorf tube and 0.5 ml of trypsin were added. In order to detach the cell from the surface of the plate, cells were incubated for the next 5 minutes. Subsequently, 1.5 ml of new culture media were added to neutralize trypsin. Cell suspension together with first solution collected were removed into 10 ml eppendorf tube and centrifuged at 1000 rpm for 5 minutes. Supernatant were removed and cell palates were suspended into 1 ml of new culture media. 100 µl of the cell suspension was dissolved in 10 ml of CASYton solution and measurement was performed.

Example 3—Construction of Disintegratable Silica Shell for Encapsulation of Cytotoxic TRAIL (APO2 Ligand) Protein (TRAIL@BS-NP)

Synthesis

Triton X-100 (1.77 mL) and n-hexanol (1.8 mL) were dissolved in Cyclohexane (7.5 mL). Separately, 100 µL of a 0.5 mg/mL aqueous solution of Human TRAIL (APO2 Ligand) were mixed with 40 µL of tetraethyl orthosilicate (TEOS) and 60 µL of bis[3-(triethoxysilyl)propyl]disulfide. After shaking, this mixture was added to the previous organic mixture. Finally, 50 µL of 30% Ammonia aqueous solution were added and the water-oil emulsion was stirred overnight at room temperature. After that, 20 mL of pure acetone were added in order to precipitate the TRAIL@BS-NP particles and the material was recovered by means of centrifugation, washing with ethanol 3 times.

If not otherwise needed, the particles were stored as a dispersion in water at 4° C.

Cellular Uptake and Cytotoxicity Study

Cell viability was measured by an automatic cell counter CASY (Roche Innovatis AG, Bielefeld, Germany). 50,000 C6 Glioma cells were grown in 2 ml of culture media inside 6 well plates at 37° C., 5% $CO_2$ environment for 24 hours. Culture media were removed and replaced by dispersion containing 0.2 mg/ml of TRAIL@BS-NP, followed by cell incubation. After 24 hours of incubation, the culture media were removed to an eppendorf tube and 0.5 ml of trypsin were added. In order to detach the cell from the surface of the plate, cells were incubated for the next 5 minutes. Subsequently, 1.5 ml of new culture media were added to neutralize trypsin. Cell suspension together with first solution collected were removed into 10 ml eppendorf tube and centrifuged at 1000 rpm for 5 minutes. Supernatant were removed and cell palates were suspended into 1 ml of new culture media. 100 μl of the cell suspension was dissolved in 10 ml of CASYton solution and measurement was performed.

Example 4—Construction of Disintegratable Silica Shell for Encapsulation of DNA Oligonucleotide Synthesis Triton X-100 (1.77 mL) and n-hexanol (1.8 mL) were dissolved in Cyclohexane (7.5 mL). Separately, 200 μL of a 300 μM aqueous solution of Cy3-DNA oligonucleotide (5'-AACAGTGAAGGAAAG-3') were mixed with 40 μL of tetraethyl orthosilicate (TEOS) and 60 μL of bis[3-(triethoxysilyl)propyl]disulfide. After shaking, this mixture was added to the previous organic mixture. Finally, 50 μL of 30% Ammonia aqueous solution were added and the water-oil emulsion was stirred overnight at room temperature.

After that, 20 mL of pure acetone were added in order to precipitate the DNA@BS-NP particles and the material was recovered by means of centrifugation, washing with ethanol 3 times.

If not otherwise needed, the particles were stored as a dispersion in water at 4° C.

Example 5—Preparation of Disintegratable Silica Shell for Encapsulation of RNAse Synthesis Synthesis of the disintegratable nanospheres was carried out following the same protocol already described for Cytochrome C and TRAIL. In this case, 300 μL of a 1.66 mg/mL solution of Onconase (20 mM Tris buffer with 0.25 M NaCl) was used, together with TEOS (40 μL) and bis[3-(triethoxysilyl)propyl]disulfide (60 μL).

If not otherwise needed, the particles were stored as a dispersion in water at 4° C.

Example 6—Preparation of NON-Disintegratable Silica Shell for Encapsulation of RNAse Synthesis The above described synthetic procedure was followed using only TEOS (100 μL) as silica agent, instead of a mixture of TEOS and bis[3-(triethoxysilyl)propyl]disulfide.

If not otherwise needed, the particles were stored as a dispersion in water at 4° C.

Results and Discussion

Figure 14:
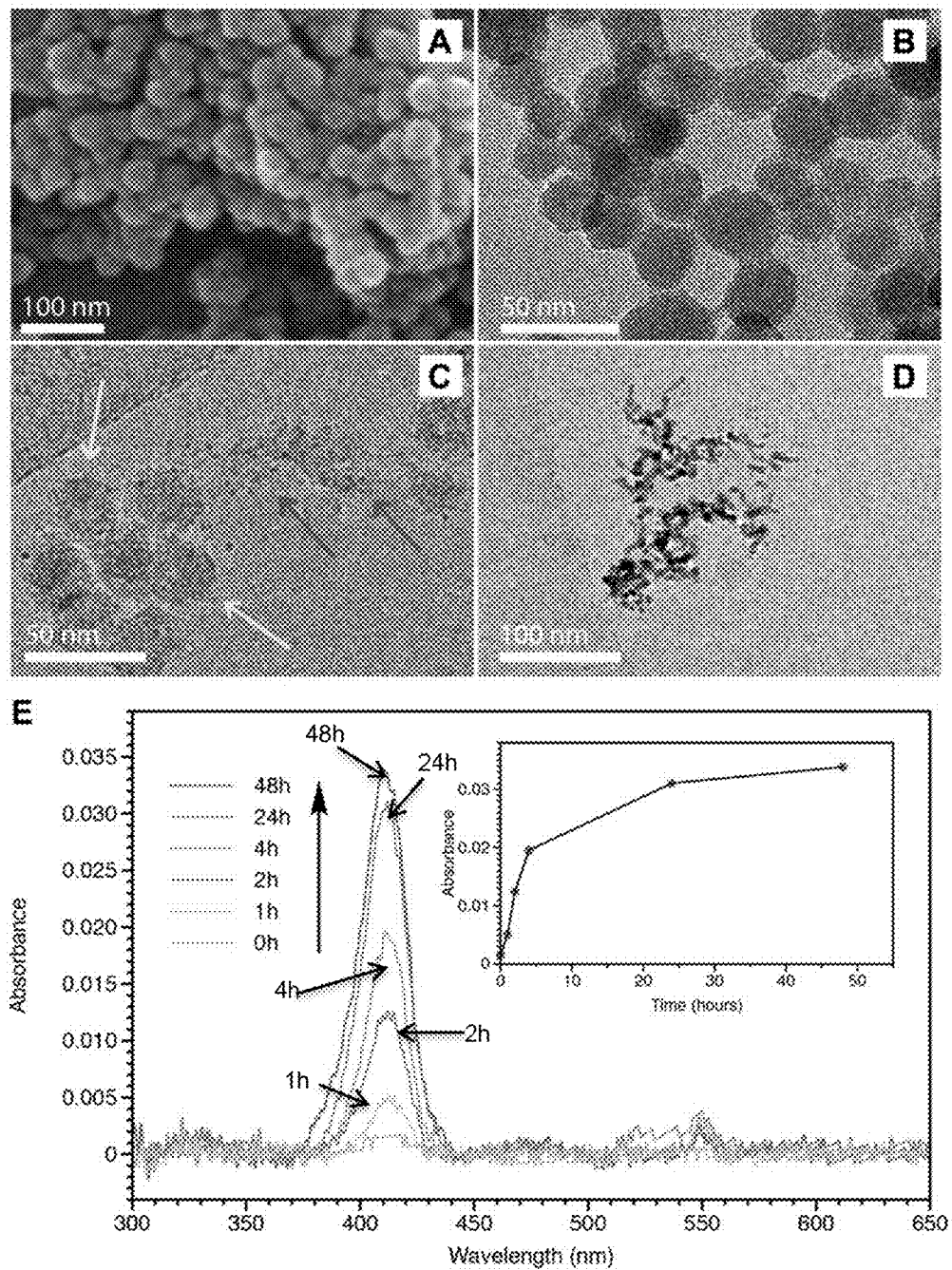
FIG. 14 provides characterization data of the material of Example 1 and release kinetics. (A) SEM image of synthesized CyC@BS-NPs, (B) HR-TEM pictures of intact CyC@BS-NPs and (C,D) cryo-TEM of the same particles after treating them with a solution of NaBH4 for 1 hour and 3 hours, respectively. (E) UV-Vis spectra of the supernatants recovered after treating CyC@BS-NPs with glutathione, in water solution. The signal monitored is due to the main electronic transition of the released cytochrome C. In the inset, release profile over time at fixed wavelength ($\lambda=410$ nm).
Figure 17:
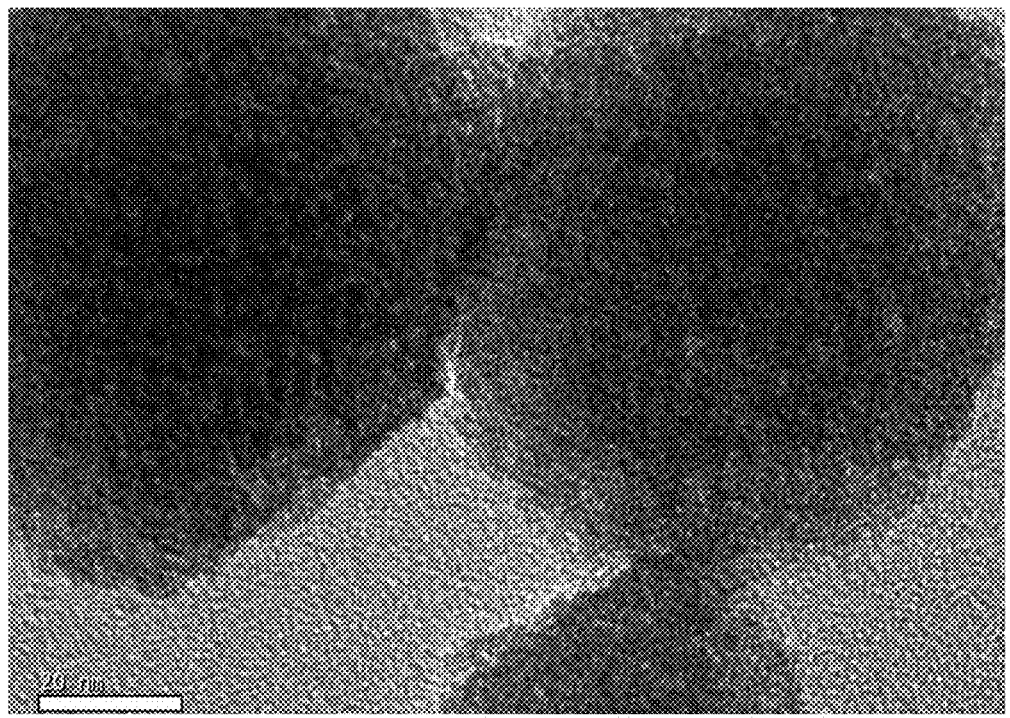
FIG. 17 HR-TEM pictures of CyC@BS-NP of Example 1.
Figure 18:
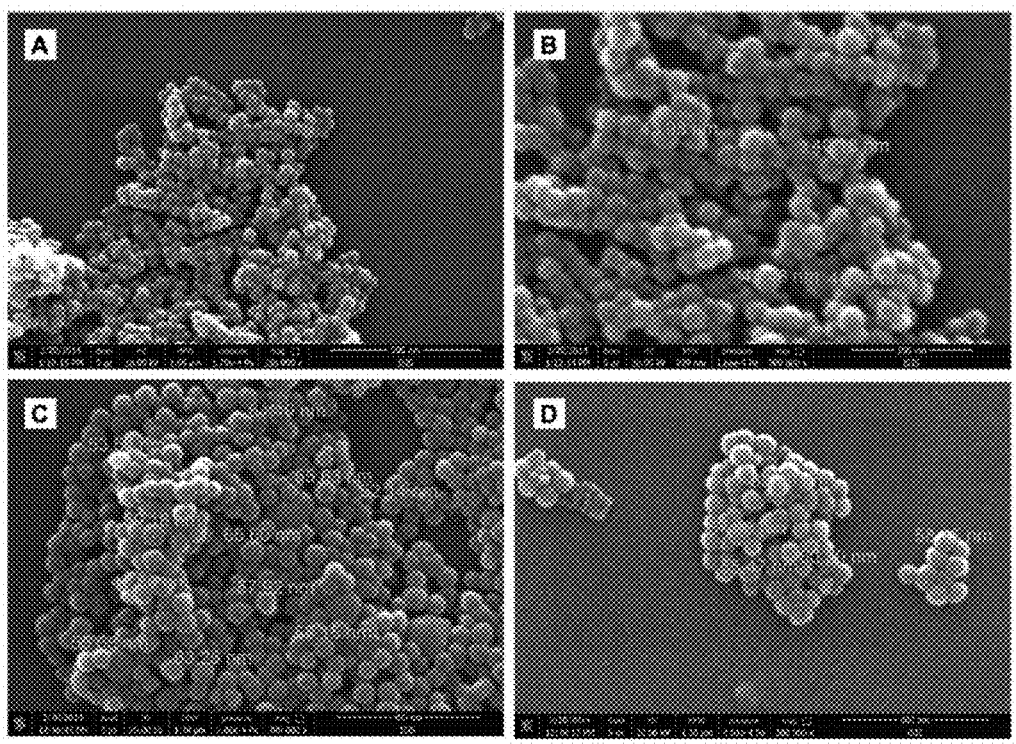
FIG. 18 Disintegratable (A,B) vs Non-disintegratable (C,D) Cytochrome C particles. The morphology of the material is retained.

As a first Example of reduction to practice of the present invention, Cytochrome C was used as a model protein, since its absorption in the visible range favors the immediate visualization of the formation of core/shell particles and enables an easy design of the release experiments that followed. The making up of the shell, in order to prevent denaturation of the biomolecule, was performed following the reverse nanoemulsion procedure described in Example 1 (see FIG. 1 for a general description). The silica network of the formed capsules contained about 30% of organic material made of the bis-propyldisulfide derivatives, which represent the redox sensitive groups. Well defined nanospheres, uniform in size, possessing a diameter around 40-50 nm were obtained (CyC@BS-NP), as shown by the SEM pictures reported in FIG. 14A. The size and the morphology of the obtained capsules have been analyzed in more details by HR-TEM measurements (FIG. 14B and FIG. 17). The material was suspended in a sodium borohydride solution and cryo-TEM images were taken after 1 hour and 3 hours exposure to the reducing agent, (FIGS. 14C and 14D) to monitor the disintegration of the capsules, due to the reduction of the disulfide groups. In an analogous manner we have prepared and analyzed non-breakable particles, lacking the S—S moieties, but containing the same protein. They show very similar structure (FIG. 18) but do not display any disintegration in the same reducing agent solution.

Figure 19:
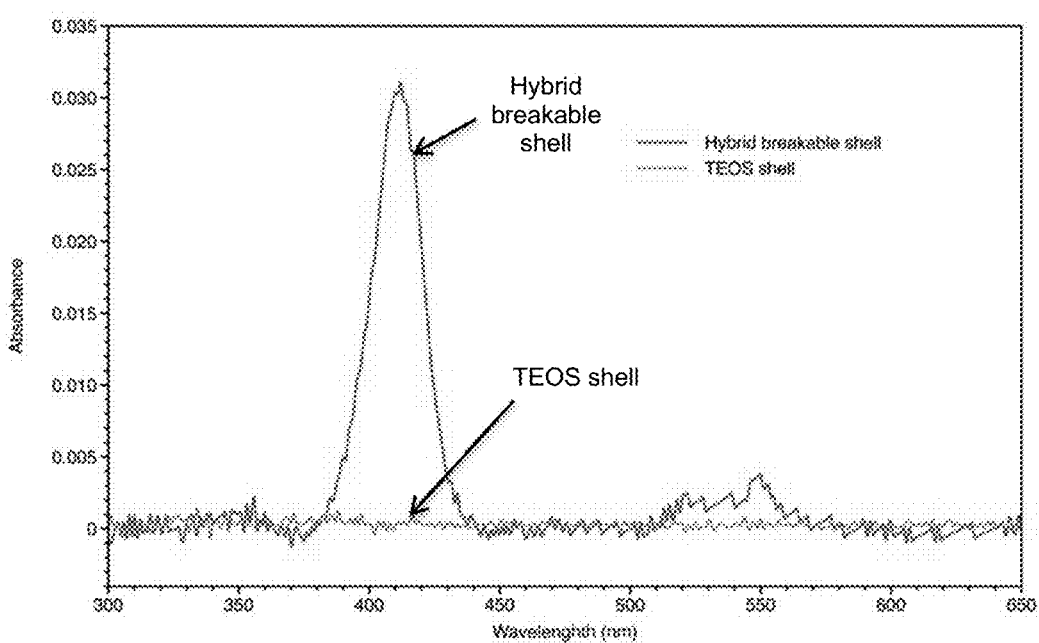
FIG. 19 UV-Vis spectra of the supernatants recovered after treating 0.5 mg/ml CyC@BS-NPs and an identical concentration of CyC@NonBS-NPs with glutathione (5 mM) for 24 h.

To evaluate the release kinetics of Cytochrome C from the disintegratable nanocapsules, upon their disintegration, the particles were dispersed in water and incubated with glutathione (5 mM, mimicking a concentration present in living cells). Analysis of the supernatant with UV-Vis spectroscopy, revealed the absorption of the Cytochrome C released from the disintegrated particles. The results summarized in plot FIG. 14E, show that at time 0 (before adding glutathione) there is no signal of the protein in solution. Upon addition of glutathione, already after 1 hour, a detectable absorption appeared at around 400 nm. The signal then increased over time, as the cytochrome C is leaving the disintegrated capsules and dissolve in water. After 24 hours the signal reaches a plateau suggesting that the escape takes place in one day and almost all the proteins are now in solution. As a control experiment we have compared the release from the non disintegratable capsules, using the same amount of cytochrome C (CyC@NonBS-NPs) observing no protein in solution even after 48 hours (FIG. 19). From the absorption feature we have also calculated the number of proteins per particle, about 31, and their almost quantitative (>90%) release from the broken capsules.

To exploit the use of these carriers in living cells, and therefore their possible application for protein delivery, we incubated the CyC@NPs with C6 Glioma cells.

Figure 15:
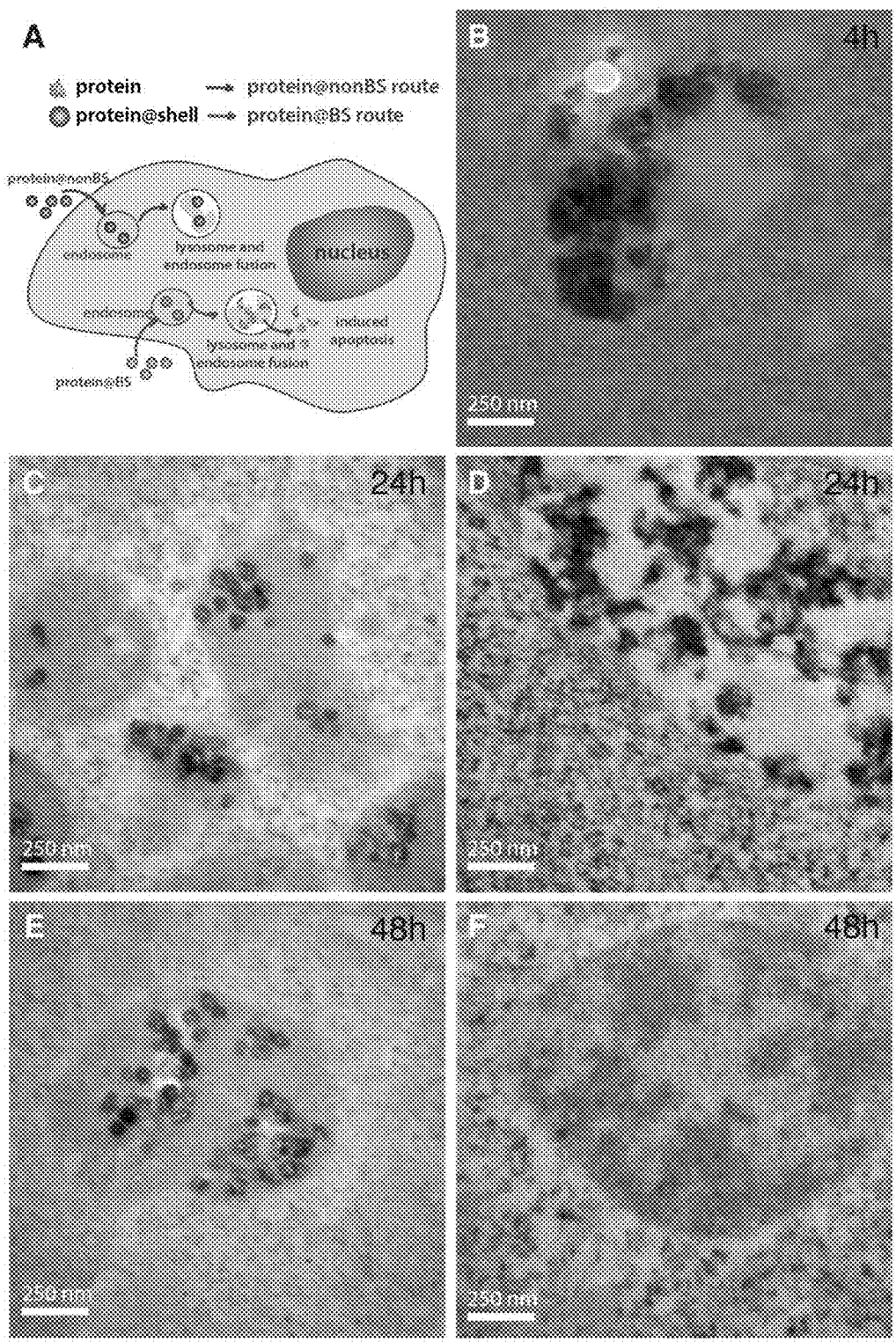
FIG. 15 represents transmission electron micrographs of internalized particles inside the cells. C6 Glioma cells were incubated for 4 and 24 hours with 0.1 mg/mL particle dispersion (CyC@BS-NPs and CyC@NonBS-NPs respectively) and cultured for additional 24 hours after changing the culture media. Panel A shows schematic representation of the nanoparticles internalization and their fate into the cell. Images B, D, F disintegratable particles, C and E non-disintegratable nanomaterials.

The disintegratable and non-disintegratable particles have been tracked using TEM measurements on fixed cells and the effect of the reducing glutathione present in the biological environment was studied in details (see FIG. 15A for a pictorial description). The experiments were carried out by analyzing the internalized particles at different incubation times i.e. 4 and 24 hours (FIGS. 15B, 15C and 15D) at concentration of particles of 0.1 mg/mL. One experiment was prolonged to 48 hours incubating the cells with the nanoparticles for 24 hours and, after washing away the particles, a further 24 hours incubation was performed in clean cell culture media (48 hours in FIGS. 15E and 15F).

TEM images clearly indicate that the nanomaterials are compartmentalized and after 4 hours even the disintegratable particles are still mostly intact. Interestingly after 24 hours the disintegration of the particles, by the lysosomal enzymatic activity, occur and only a multitude of amorphous morphologies are detectable, FIG. 15D. The destruction of the organosilica shell is complete after 48 hours, and aggregated debris, that give a diffuse contrast to the lysosome, is observed (FIG. 15F). The non disintegratable particles do not show any degradation even after 48 hours incubation maintaining the typical round shape (FIGS. 15C and 15E) as the fresh-synthesized ones (FIG. 14B).

Figure 20:
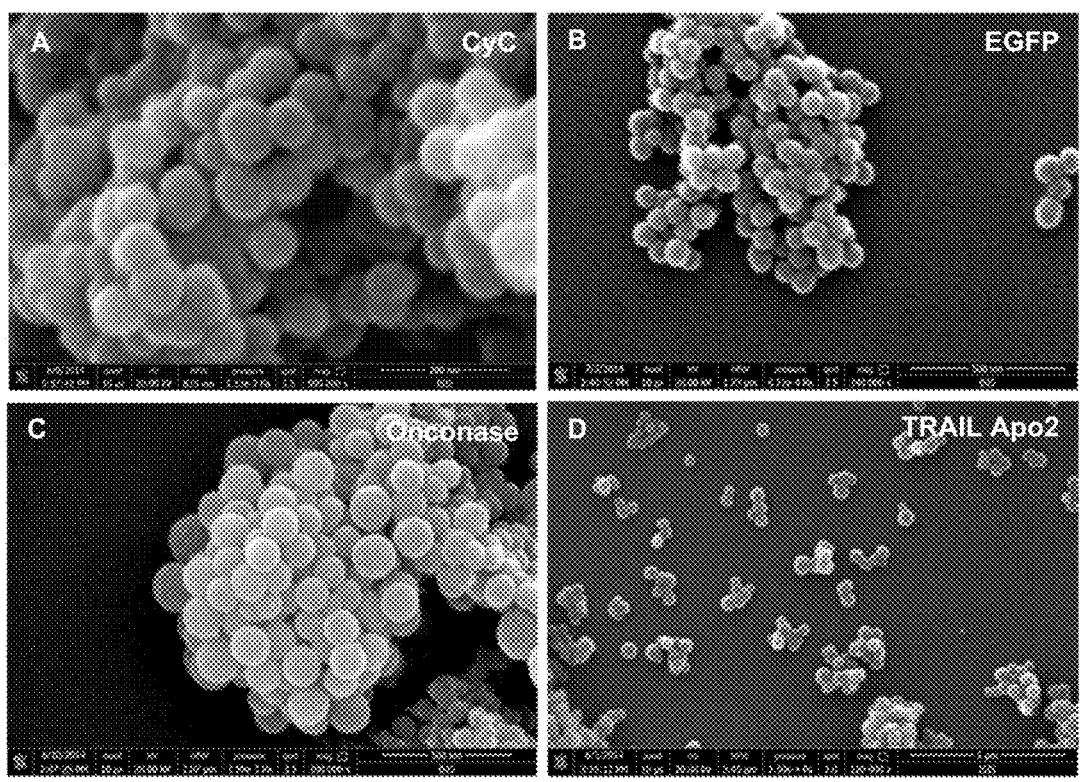
FIG. 20 SEM pictures of CyC@BS-NP (A), EGFP@BS-NP (B), Onconase@BS-NP (C), TRAIL@BS-NP (D).
Figure 21:
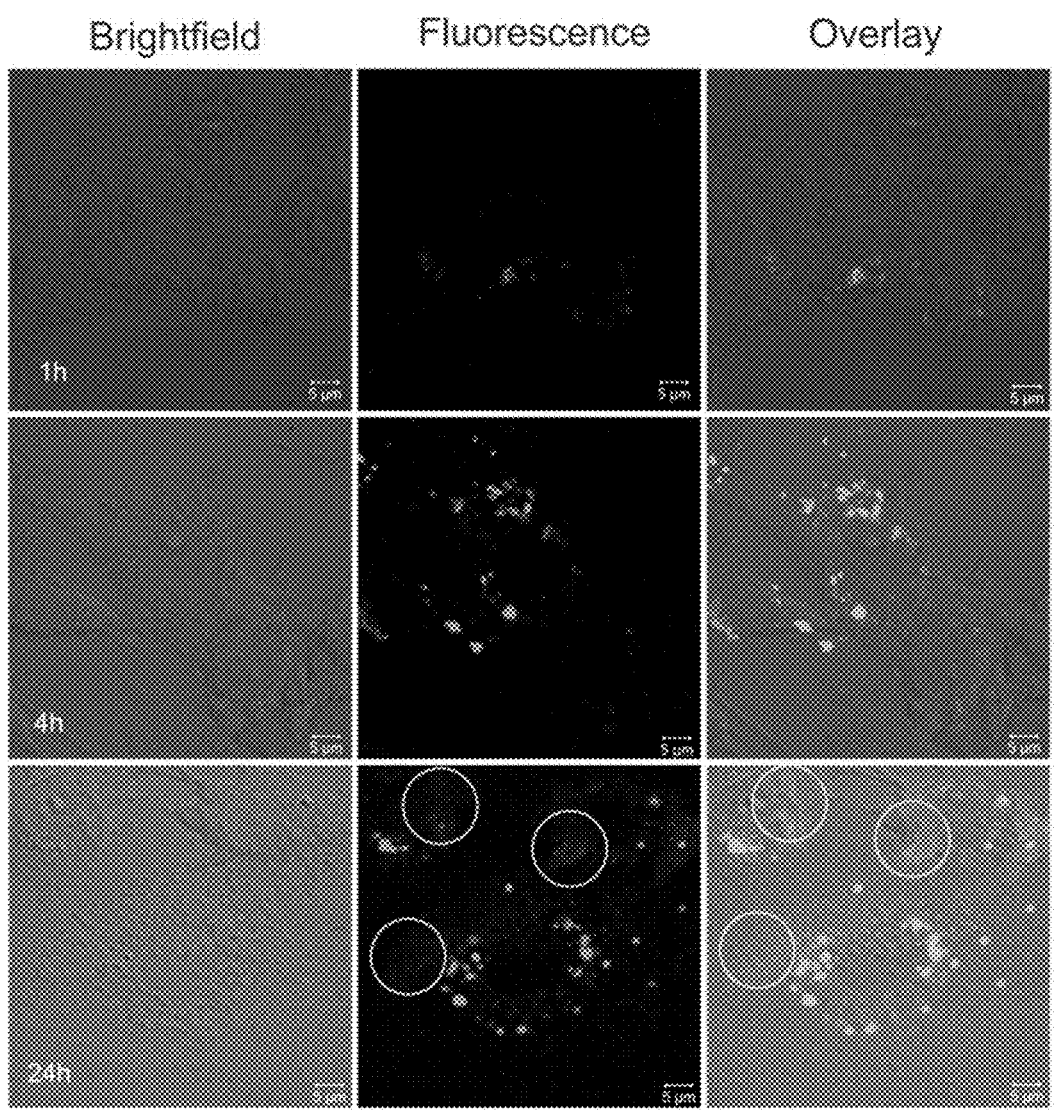
FIG. 21 Confocal microscopy images showing the kinetics of internalization and distribution EGFP-encapsulated disintegratable silica shells in C6 Glioma cells. The cells were incubated with the modified particles for different incubation times: 1, 4, and 24 hours (concentration 0.05 mg in 1 ml of culture media) followed by 10× washing treatment using PBS buffer and cellular fixation using 4% PFA solution. Green corresponds to EGFP. Excitation wavelength is 488 nm for EGFP. Emissions were recorded in the range of EGFP emission band. Scale bars=5 □m.
Figure 22:
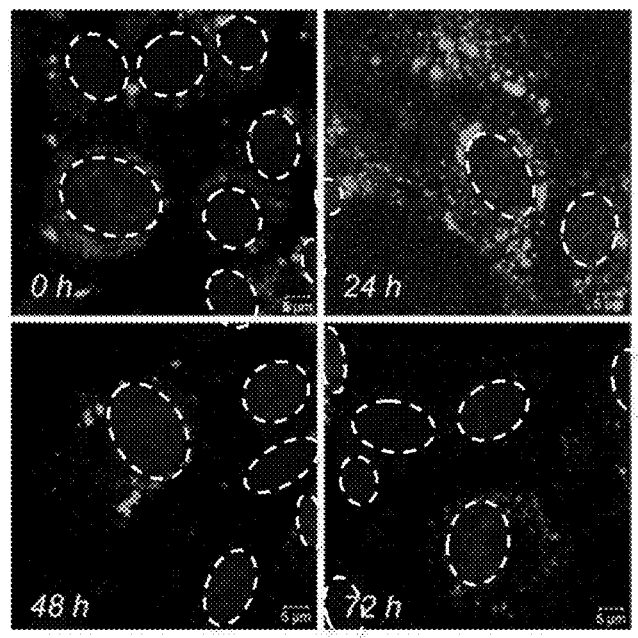
FIG. 22 Confocal microscopy images showing the kinetics of biodegradation and distribution EGFP-encapsulated disintegratable silica shells in C6 Glioma cells. The cells were incubated with the modified particles for 4 hours (concentration 0.2 mg/ml) followed by 10× treatment using PBS buffer. Imaging experiments were done directly after incubation, after 1 day, after 2 days, and after 3 days. Blue color (areas indicated by dotted circles/ovals on black & white photograph) is indicating signal from Hoechst 33342 stains cells' nucleus and green (light grey spots on black & white photograph) corresponds to EGFP. Excitation wavelengths=405 and 488 nm for Hoechst 33342 and EGFP, respectively. Emissions were recorded with a Hoechst 33342 emission filter and an EGFP emission filter, respectively. Scale bars=5 Ξm.

In order to visualize and co-localize the particles, we have encapsulated in the breakable capsules fluorescent proteins, EGFPs as probe for the confocal microscope, and also to prove that encapsulation can occur with different type of proteins (FIG. 20). Incubation of the EGFP@BS-NP with C6 Glioma cells (see FIGS. 16A and 16B), showed co-localization into the lysosome and the degradation results are in accordance with the breaking behavior observed so far by TEM for the CyC@BS-NP. In this case the release of EGFP into the cytoplasm results in a diffuse non-co-localized emission signal because of the spreading of the fluorescent proteins into the cell (see FIGS. 21 and 22).

To demonstrate that the shell is protecting and maintaining the activity of the macrobiomolecules intact, we have then encapsulated toxic proteins such as Human TRAIL APO2 Ligand (TRAIL@BS-NP) and Onconase (Onconase@BS-NP) in disintegratable shell nanocapsules (FIG. 20), and incubated the nanomaterials with cells.

Figure 16:
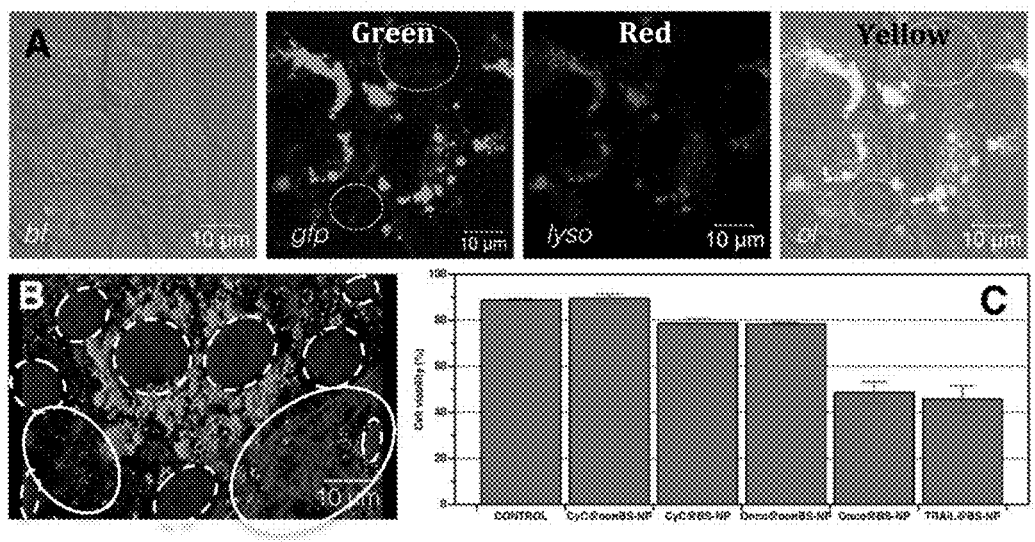
FIG. 16 (A) Confocal micrographs taken after 24 h incubation with the particles (concentration 0.05 mg/mL) showing the localization of the particles in C6 Glioma cells. Co-localization experiments with LysoTracker® Red DND-99 revealed the sublocalization of particles in lysosome area (overlap coefficient 0.87). Green color is indicating signal from EGFP, red corresponds to lysosome, yellow circle pointing the non co-localized area of released EGFP with lysosome. Scale bars=10 µm. (B) Top view of 3D confocal microscopy image of f-actin (red, main areas indicated by plain circles/ovals) and nucleus stained (blue, areas indicated with dotted circles/ovals) C6 cells uptaking EGFP-containing particles (light grey). Excitation wavelengths are 405, 488, 594, and 633 nm for DAPI, EGFP, LysoTracker® Red DND-99, and Alexa Fluor® 647 Phalloidin, respectively. (C) summary of cell viability tests.

TRAIL Apo2 Ligand is a protein that belongs to the tumor necrosis factor (TNF) family of death ligands and can be used to overcome resistance to conventional chemotherapeutic drugs. TRAIL@BS-NPs were thus initially tested on a C6 Glioma cell line, and toxicity can be expected only when the protein is delivered into the cytosol in its native folding. To have a full quantification of the toxicity of the material we have also investigated the same type and number of cells after incubation with the potentially non-toxic CyC@BS-NP and CyC@NonBS-NPs. The overall cell viability was measured as direct indicator of the cytotoxic/anticancer effect provided by the hybrid particles. The results are summarized in the plot in FIG. 16 and show that CyC@NonBS-NPs did not influence the total cell viability with respect to the control culture, meaning that the core/shell system is absolutely biocompatible and non-cytotoxic (FIG. 16C). In the case of CyC@BS-NPs, a slight reduction of the viability was registered (78.7% vs 89.5% control), which can be possibly ascribed to an interference effect in the normal biological metabolism due to an excess of cytochrome C present in the cell after the delivery, inducing apoptosis. [11]

Figure 23:
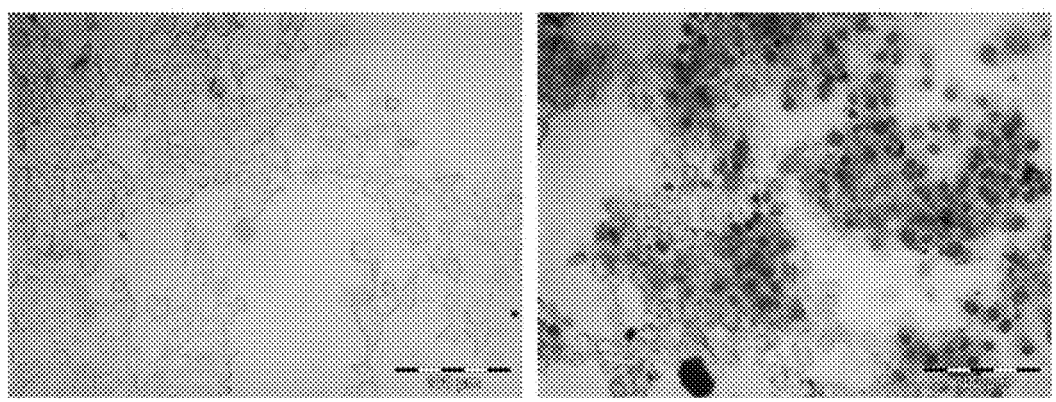
FIG. 23 Trypan blue cell mortality test performed after 24 hours of incubation for C6 glioma cells. Left) Control sample (pure cell culture), which shows the dye does not stain healthy cells; right) sample treated with 0.15 mg/ml TRAIL@BS-NP. Dead cells are visualized in blue after interaction with trypan blue.

An important result, displayed in FIG. 16C, is the cell viability percentage obtained when treating the C6 Glioma cells with TRAIL@BS-NP (0.15 mg/mL, 24 h), which induced a drastic reduction of the value up to 45% with respect to the control sample. The results highlight the effective role of the nanosphere system internalized by the cell: able to deliver the protein in the native form upon degradation of the outer shell. The released TRAIL must be in an active conformation to carry on its apoptosis inducing effect, as indicated by the overall cell viability reduction. To confirm this effect, the same TRAIL@BS-NPs were also used to incubate C6 Glioma cells under the same conditions, which were eventually analyzed through Trypan blue cell mortality test. Trypan blue is a dye that allows to selectively stain dead cells, depending on the rupture of the cell membrane that enables its cell penetration, while live healthy cells are completely impermeable and blind to this test. The results are reported in FIG. 23 and show perfect accordance with the viability test.

The role played by the breakable disulfide contained shell and its potential as chemotherapeutic tool was corroborated when viability experiments were conducted on the same cell line using Onconase@BS-NP and compared with the non-breakable nanoparticles, Onconase@NonBS-NP. The nanomaterials were synthesized and incubated with the same cell line. The cytotoxicity experiments were then performed as aforementioned, and once again the cell viability was employed to evaluate the integrity of the protein and its activity as cell inducing apoptosis. It is important to note that Onconase@NonBS-NP did not affect the cell viability, as no significant change could be registered with respect to the control sample, FIG. 16C. The excellent biocompatibility of the material is also an indicator that the protein cargo cannot leak out when the nanocapsule shell is made entirely of silica, and the selected proteins are not present on the silica surface. On the other hand, when treating the cells with Onconase@BS-NP (0.15 mg/mL, 24 h), a dramatic drop of the viability percentage was obtained, up to 40%. This demonstrates that the delivery of Onconase occurs upon degradation of the breakable shell. The data strongly suggest that the Onconase was thus released in its functional conformation, able to carry on its related anti-tumor effect.

The general method for the encapsulation of proteins and enzymes within a stimulus-responsive breakable hybrid organo-silica shell can open important venues to the treatment of several diseases caused by the lack or low expression of enzymes, proteins, and other biomolecules.

While we have described a number of embodiments of this invention, it is apparent that our basic examples may be altered to provide other embodiments that utilize the catalysts and methods of this invention. Therefore, it will be appreciated that the scope of this invention is to be defined by the appended claims rather than by the specific embodiments that have been represented by way of example.

LIST OF REFERENCES

[1] S. J. Rowan, S. J. Cantrill, G. R. L. Cousins, J. K. M. Sanders, J. F. Stoddart, Angew. Chem. Int. Ed., 2002, 41, 898.
[2] K. J. Shea, D. A. Loy, Chem. Mater. 2001, 13, 3306.
[3] J. Pyun, S. Jia, T. Kowalewski, G. D. Patterson, K. Matyjaszewski, Macromolecules, 2003, 36, 5094-5104;
[4] C. Sanchez, B. Julian, P. Belleville, M. Popall, J. mater. Chem. 2005, 15, 3559-3592;
[5] S. R. Hall, S. S. Davis, S. Mann, Langmuir, 2000, 16, 1454-1456.
[6] Inagaki, S.; Guan, S.; Ohsuna, T.; Terasaki, O. *Nature* 2002, 416, 304-307.
[7] Asefa, T.; MacLachlan, M. J.; Coombs, N.; Ozin, G. A. *Nature* 1999, 402, 867-871.
[8] M. Graffner-Nordberg, K. Sjödin, A. Tunek, A. Hallberg, Chem. Pharm. Bull., 1998, 46, 591.
[9] M. Kobayashi, Y. Fujiwara, M. Goda, H. Komeda, S. Shimizu, PNAS, 1997, 94, 11986.
[10] C. Lopreore, L. D. Byers, Arch. Biochem. Biophys., 1998, 349, 299.
[11] R. M. Kluck, E. Bossy-Wetzel, D. R. Green, D. D. Newmeyer, Science 1997, 275, 1132-1136.

All patent(s) and publication(s) mentioned in this specification are herein incorporated by reference to the same extent as if each individual publication was specifically and individually indicated to be incorporated by reference.

TABLE 3

| Sample Name | Zeta Potential (mV) |
| --- | --- |
| CyC@BS-NP | −17.67 |
| TRAIL@BS-NP | −8.86 |
| DNA@BS-NP | −15.48 |

TABLE 4

| | 24 h | | | | |
| --- | --- | --- | --- | --- | --- |
| | 1$^{st}$ (%) | 2$^{nd}$ (%) | 3$^{rd}$ (%) | AVE (%) | ST. DEV. |
| TRAIL@BS-NP | 52.5 | 42.4 | 42.5 | 45.8 | 5.80 |
| Onco@nonBS-NP | 77.7 | 78.5 | 79 | 78.4 | 0.66 |
| Onco@BS-NP | 44.5 | 47.8 | 53.6 | 48.6 | 4.6 |
| CyC@BS-NP | 80.9 | 77.5 | 77.8 | 78.7 | 1.88 |
| CyC@nonBS-NP | 91.7 | 87.9 | 88.9 | 89.5 | 1.96 |
| CONTROL | 88 | 89.3 | 88.8 | 88.7 | 0.65 |

The invention claimed is:

1. A nanoencapsulated bioactive macromolecule or bioactive macromolecule cluster, consisting essentially of:
   (a) a disintegratable nanocapsule having a core/shell structure, wherein the shell of the nanocapsule is made of hybrid organosilica material comprising a three-dimensional framework of Si—O bonds, wherein at least a subset of Si atoms in the framework is connected to at least another Si atom in the framework through a linker having the following structure:

*—R$^1$—L-R$^2$—*;

wherein:
   each occurrence of * denotes a point of attachment to a Si atom in the framework;
   L represents a responsively cleavable covalent bond, and R$^1$ and R$^2$ independently represent an optionally substituted C1-20 alkylenyl moiety, an optionally substituted C1-20 heteroalkylenyl moiety, an optionally substituted ethylenyl moiety, —C≡C— or an optionally substituted phenyl moiety, wherein the C1-20 alkylenyl, C1-20 heteroalkylenyl or ethylenyl moiety may bear one or more substituents selected from halogen or OR where R may represent H or C1-6alkyl, and the phenyl moiety may bear one or more substituents independently selected from halogen, C1-6 alkyl, —NO$_2$, —CN, isocyano, —OR$^P$, —N(R$^P$)$_2$ wherein each occurrence of R$^P$ independently represents H or C1-6 alkyl; and
   (b) a bioactive macromolecule or bioactive macromolecule cluster encapsulated within the nanocapsule, wherein the bioactive macromolecule(s) within the nanocapsule is/are in a conformation to carry on supposed biological activity of the bioactive macromolecule(s); and
   wherein the nanocapsule inner core does not contain a micellar phase.

2. The nanoencapsulated bioactive macromolecule of claim 1, wherein the linker has the structure *—R$^1$—L—R$^2$—*, and L represents a responsively cleavable covalent bond selected from:

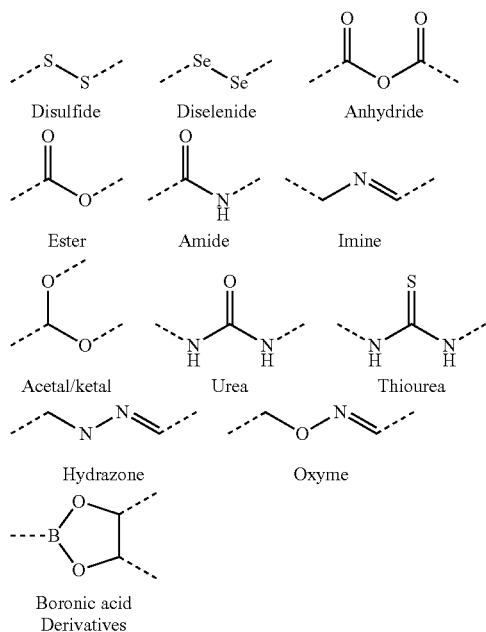

3. The nanoencapsulated bioactive macromolecule of claim 1, wherein in the linker having the structure*—R$^1$—L—R$^2$—*, and R$^2$ are identical, and each represent CH$_2$—, —(CH$_2$)$_2$—, —(CH$_2$)$_3$—, —(CH$_2$)$_4$—, or phenyl.

4. The nanoencapsulated bioactive macromolecule of claim 1, wherein the macromolecule is selected from the group consisting of proteins, enzymes, antibodies, peptides, DNA, RNA, and gene fragments.

5. The nanoencapsulated bioactive macromolecule of claim 1, wherein the nanocapsule shell has a diameter between 25 nanometers and 500 nanometers.

6. The nanoencapsulated bioactive macromolecule of claim 1, wherein the nanocapsule shell is disintegratable as a stimulus is applied, and the supposed biological activity of the macromolecule(s) remain(s).

7. The nanoencapsulated bioactive macromolecule of claim 1, wherein the nanocapsule shell is disintegratable as a stimulus is applied, and the supposed biological activity of the macromolecule remains, wherein the stimulus is selected from a change in pH (either an increase or decrease), a change in redox potential, the presence of reduction or oxidation agent, the presence of UV light or near infrared light, an enzymatic cleavage, or a change in temperature.

8. The nanoencapsulated bioactive macromolecule of claim 1, further functionalized at its outer surface with PEG, antibody, or RNA moieties.

9. A pharmaceutical or cosmetic composition comprising:
   a nanoencapsulated bioactive macromolecule consisting essentially of:
   (a) a disintegratable nanocapsule having a core/shell structure, wherein the shell of the nanocapsule is made of hybrid organosilica material comprising a three-dimensional framework of Si—O bonds, wherein at least a subset of Si atoms in the framework is connected to at least another Si atom in the framework through a linker having the following structure:

*—R$^1$—L-R$^2$—*;

wherein:
   each occurrence of * denotes a point of attachment to a Si atom in the framework;
   L represents a responsively cleavable covalent bond, and R$^1$ and R$^2$ independently represent an optionally substituted C1-20 alkylenyl moiety, an optionally substituted C1-20 heteroalkylenyl moiety, an optionally substituted ethylenyl moiety, —C≡C— or an optionally substituted phenyl moiety, wherein the C1-20 alkylenyl, C1-20 heteroalkylenyl or ethylenyl moiety may bear one or more substituents selected from halogen or —OR where R may represent H or C1-6alkyl, and the phenyl moiety may bear one or more substituents independently selected from halogen, C1-6 alkyl, —NO$_2$, —CN, isocyano, —OR$^P$, —N(R$^P$)$_2$ wherein each occurrence of R$^P$ independently represents H or C1-6 alkyl; and
   (b) a bioactive macromolecule or bioactive macromolecule cluster encapsulated within the nanocapsule, wherein the bioactive macromolecule(s) within the nanocapsule is/are in a conformation to carry on supposed biological activity of the bioactive macromolecule(s); and
   a pharmaceutically or cosmetically acceptable carrier, wherein the nanocapsule inner core does not contain a micellar phase.

10. A method for preparing a nanoencapsulated bioactive macromolecule of claim 1, comprising:

(a) producing a water-in-oil emulsion from (i) a solution of a suitable surfactant other than a phospholipid and alcohol in a suitable organic solvent, and (ii) an aqueous solution of a bioactive macromolecule or bioactive macromolecule clusters, a silane precursor $Si(X^A)_4$ and a selected precursor having the structure $(X)_3Si-R^1-L-R^2-Si(X)_3$;

(b) stirring the water-in-oil emulsion obtained in step (a) under alkaline conditions; thereby coating the bioactive macromolecule or bioactive macromolecule clusters with an organosilica sol-gel mixture obtained by hydrolysis-condensation of silicon alkoxide; and (c) adding a suitable organic solvent, thereby precipitating the nanoencapsulated bioactive macromolecules or bioactive macromolecule clusters:

wherein:

each occurrence of X and $X^A$ independently represents a hydrolysable or nonhydrolyzable group, provided that on each occurrence of Si of the precursor $(X)_3Si-R^1-L-R^2-Si(X)_3$, at least one occurrence of X represents a hydrolysable group, and at least two occurrences of $X^A$ in the precursor $Si(X^A)_4$ independently represent a hydrolysable group; wherein (i) when X or $X^A$ represents a nonhydrolyzable group, it may be selected from an optionally substituted C1-20 alkyl, C2-20 alkenyl or C2-20 alkynyl moiety, an optionally substituted C1-20 heteroalkyl, C2-20 heteroalkynyl or C2-20 heteroalkynyl moiety, or an optionally substituted phenyl moiety, wherein the substituents on the phenyl, alkyl, alkenyl, alkynyl, heteroalkyl, heteroalkenyl and heteroalkynyl moieties may be independently selected from halogen, $-NO_2$, $-CN$, isocyano, C1-6 alkoxy, an oxirane/epoxyde moiety, $-N(R)_2$ wherein each occurrence of R is independently selected from H or C1-6 alkyl; and (ii) when X or $X^A$ represents a hydrolysable group, it may be selected from a C1-6 alkoxy, C1-6 acyloxy, halogen or amino moiety;

L represents a responsively cleavable covalent bond; and $R^1$ and $R^2$ independently represent an optionally substituted C1-20 alkylenyl moiety, an optionally substituted C1-20 heteroalkylenyl moiety, an optionally substituted ethylenyl moiety, $-C\equiv C-$ or an optionally substituted phenyl moiety, wherein the C1-20 alkylenyl, C1-20 heteroalkylenyl or ethylenyl moiety may bear one or more substituents selected from halogen or $-OR$ where R may represent H or C1-6 alkyl, and the phenyl moiety may bear one or more substituents independently selected from halogen, C1-6alkyl, $-NO_2$, $-CN$, isocyano, $-OR^P$, $-N(R^P)_2$ wherein each occurrence of $R^P$ independently represents H or C1-6 alkyl.

11. The method of claim 10, wherein $Si(X^A)_4$ represents a tetraalkoxysilane.

12. The method of claim 10, wherein the surfactant is a nonionic surfactant.

13. The method of claim 10, wherein the alcohol is methanol, ethanol, propanol, isopropanol, n-butanol, tert-butanol or hexanol.

14. The method of claim 10, wherein the linker comprises one of the following bonds:

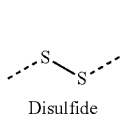
Disulfide

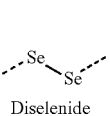
Diselenide

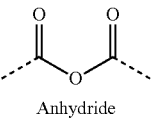
Anhydride

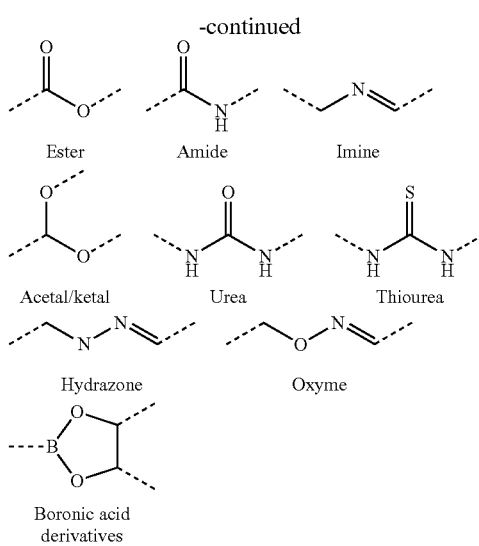

15. The method of claim 10, wherein the precursor having the structure $(X)_3Si-R^1-L-R^2-Si(X)_3$ is produced in situ.

16. A method for systemically delivering a bioactive macromolecule, in a biologically active form, to a subject in need thereof, the method comprising, administering to the subject a therapeutically effective amount of a nanoencapsulated bioactive macromolecule or bioactive macromolecule cluster of claim 1.

17. The method of claim 16, wherein the bioactive macromolecule is selected from the group consisting of proteins, oligonucleotides, antibodies, peptides, PNA, DNA, RNA, gene fragments, a hormone, a growth factor, a protease, an extra-cellular matrix protein, an enzyme, an infectious viral protein, an antisense oligonucleotide, a dsRNA, a ribozyme and a DNAzyme.

18. The method of claim 16, wherein the bioactive macromolecule is an enzyme and the biological activity is a catalytic activity.

19. The method of claim 16, wherein the bioactive macromolecule is a hormone and the biological activity is a ligand binding activity.

20. A unit dosage form for local delivery of a bioactive macromolecule to a tissue of a subject, the unit dosage form comprising, a therapeutically effective amount of a nanoencapsulated bioactive macromolecule or bioactive macromolecule cluster consisting essentially of:

(a) a disintegratable nanocapsule having a core/shell structure, wherein the shell of the nanocapsule is made of hybrid organosilica material comprising a three-dimensional framework of Si—O bonds, wherein at least a subset of Si atoms in the framework is connected to at least another Si atom in the framework through a linker having the following structure:

wherein:

each occurrence of * denotes a point of attachment to a Si atom in the framework;

L represents a responsively cleavable covalent bond, and $R^1$ and $R^2$ independently represent an optionally substituted C1-20 alkylenyl moiety, an optionally substituted C1-20 heteroalkylenyl moiety, an optionally substituted ethylenyl moiety, $-C\equiv C-$ or an optionally substituted phenyl moiety, wherein the C1-20 alkylenyl, C1-20 heteroalkylenyl or ethylenyl moiety may bear one or more substituents selected from halogen or —OR where R may represent H or C1-6alkyl, and the phenyl moiety may bear one or more substituents independently selected from halogen, C1-6 alkyl, —NO$_2$, —CN, isocyano, —OR$^P$, —N(R$^P$)$_2$ wherein each occurrence of R$^P$ independently represents H or C1-6 alkyl; and (b) a bioactive macromolecule or bioactive macromolecule cluster encapsulated within the nanocapsule, wherein the bioactive macromolecule(s) within the nanocapsule is/are in a conformation to carry on supposed biological activity of the bioactive macromolecule(s); and wherein the nanocapsule inner core does not contain a micellar phase; and wherein the macromolecule is selected from the group consisting of proteins, oligonucleotides, antibodies, peptides, PNA, DNA, RNA, gene fragments, a hormone, a growth factor, a protease, an extra-cellular matrix protein, an enzyme, an infectious viral protein, an antisense oligonucleotide, a dsRNA, a ribozyme and a DNAzyme.

21. A method for treating a disease in a subject-in-need thereof, the method comprising administering to the subject a therapeutically effective amount of a nanoencapsulated bioactive macromolecule or bioactive macromolecule cluster of claim 1 or a pharmaceutical composition thereof, thereby treating the disease in the subject.

22. A delivery system for enhancing the circulation time of a bioactive macromolecule of therapeutic interest in vivo, the system comprising a nanoencapsulated bioactive macromolecule or bioactive macromolecule cluster consisting essentially of:

(a) a disintegratable nanocapsule having a core/shell structure, wherein the shell of the nanocapsule is made of hybrid organosilica material comprising a three-dimensional framework of Si—O bonds, wherein at least a subset of Si atoms in the framework is connected to at least another Si atom in the framework through a linker having the following structure:

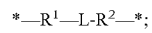

wherein:
each occurrence of * denotes a point of attachment to a Si atom in the framework;

L represents a responsively cleavable covalent bond, and R$^1$ and R$^2$ independently represent an optionally substituted C1-20 alkylenyl moiety, an optionally substituted C1-20 heteroalkylenyl moiety, an optionally substituted ethylenyl moiety, —C≡C— or an optionally substituted phenyl moiety, wherein the C1-20 alkylenyl, C1-20 heteroalkylenyl or ethylenyl moiety may bear one or more substituents selected from halogen or —OR where R may represent H or C1-6alkyl, and the phenyl moiety may bear one or more substituents independently selected from halogen, C1-6 alkyl, —NO$_2$, —CN, isocyano, —OR$^P$, —N(R$^P$)$_2$ wherein each occurrence of R$^P$ independently represents H or C1-6 alkyl; and (b) a bioactive macromolecule or bioactive macromolecule cluster encapsulated within the nanocapsule, wherein the bioactive macromolecule(s) within the nanocapsule is/are in a conformation to carry on supposed biological activity of the bioactive macromolecule(s); and wherein the nanocapsule inner core does not contain a micellar phase; and wherein the thickness of the nanocapsule shell is adapted to deliver the encapsulated bioactive macromolecule of therapeutic interest into in vivo circulation at a controlled rate of release.

* * * * *